US009987296B2

(12) United States Patent
Johnson

(10) Patent No.: US 9,987,296 B2
(45) Date of Patent: *Jun. 5, 2018

(54) COMPOSITIONS INCLUDING ANTHOCYANIN OR ANTHOCYANIDIN FOR THE PREVENTION OR TREATMENT OF ARTICULAR CARTILAGE-ASSOCIATED CONDITIONS

(71) Applicant: Lanny Johnson, Frankfort, MI (US)

(72) Inventor: Lanny Johnson, Frankfort, MI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/273,186

(22) Filed: Sep. 22, 2016

(65) Prior Publication Data

US 2017/0007634 A1 Jan. 12, 2017

Related U.S. Application Data

(63) Continuation of application No. 13/568,651, filed on Aug. 7, 2012, now Pat. No. 9,486,468, which is a continuation of application No. 12/651,415, filed on Dec. 31, 2009, now Pat. No. 8,263,069.

(60) Provisional application No. 61/142,070, filed on Dec. 31, 2008.

(51) Int. Cl.
| A01N 63/00 | (2006.01) |
| A61K 31/7048 | (2006.01) |
| A61K 9/00 | (2006.01) |
| A61K 31/352 | (2006.01) |
| A61K 45/06 | (2006.01) |
| C12N 5/077 | (2010.01) |
| A61K 9/16 | (2006.01) |

(52) U.S. Cl.
CPC ........ *A61K 31/7048* (2013.01); *A61K 9/0019* (2013.01); *A61K 9/16* (2013.01); *A61K 31/352* (2013.01); *A61K 45/06* (2013.01); *C12N 5/0655* (2013.01); *C12N 2501/105* (2013.01); *C12N 2501/23* (2013.01)

(58) Field of Classification Search
None
See application file for complete search history.

(56) References Cited

U.S. PATENT DOCUMENTS

| 4,997,850 | A | 3/1991 | Kimura et al. |
| 5,304,205 | A | 4/1994 | Shinoda et al. |
| 6,315,992 | B1 | 11/2001 | Noh et al. |
| 7,575,743 | B2 | 8/2009 | Hunziker |
| 8,263,069 | B2 * | 9/2012 | Johnson ............... A61K 9/0019 424/93.1 |
| 9,486,468 | B2 * | 11/2016 | Johnson ............... A61K 9/0019 |
| 2002/0058614 | A1 * | 5/2002 | Filvaroff .............. A61K 9/5031 514/6.5 |
| 2004/0105878 | A1 | 6/2004 | Schwendeman et al. |
| 2004/0127459 | A1 | 7/2004 | Dehayza et al. |
| 2006/0025354 | A1 | 2/2006 | Nair et al. |
| 2006/0040894 | A1 | 2/2006 | Hunter et al. |
| 2006/0051327 | A1 | 3/2006 | Johnson |
| 2006/0210552 | A1 | 9/2006 | Demopulos et al. |
| 2006/0234957 | A1 | 10/2006 | Tsuda et al. |
| 2006/0258588 | A1 | 11/2006 | Pike et al. |
| 2007/0020237 | A1 | 1/2007 | Yoon et al. |
| 2007/0021496 | A1 | 1/2007 | Terkeltaub et al. |
| 2008/0200559 | A1 | 8/2008 | Kannar et al. |

FOREIGN PATENT DOCUMENTS

JP 08104628 4/1996

OTHER PUBLICATIONS

Pergola et al. Nitric Oxide (2006) 15: 30-39.*
Jozeau et al. Osteoarthritis and Cartilage (1999) 7: 382-385.*
Wang et al. J. Agric. Food Chem. (2002) 50: 850-857.*
Toskangerpoll et al. (Food Chem. (2005) 89: 427-440 (Year: 2005).*
Machine translation of JP 08104628, downloaded Apr. 25, 2013 from the JPO.
Aldrich Catalog (1996) p. 1221.
Ahmed et al., "*Punica granatum* L. extract inhibits IL-1beta-induced expression of matrix metalloproteinases by inhibiting the activation of MAP kinases and NF-kappaB in human chondrocytes in vitro" J. Nutr. (2005) 135:2096-2102.
Defintion of dextrose from http://medical-dictionary.thefreedictionary.com/dextrose, download Feb. 20, 2014.
Du et al., "Anthocyanins of Pomegranate, Punica granatum" J. Food Science (1975) 40(2): 417-18.
Kim et al., "Mulberry Extract Supplements Ameliorate the Inflammation-Related Hematological Parameters in Carrageenan-Induced Arthritic Rats" J. Medicinal Food (2006) 9(3): 431-435.
Liggins et al. "Intra-articular treatment of arthritis with microsphere formulations of paclitaxel: biocompatibility and efficacy determinations in rabbits" Inflamm. Res. (2004) 53: 363-372.
Marks, R. "Obesity Profiles with Knee Osteoarthritis: Correlation with Pain, Disability, Disease Progression" Obesity (Jul. 2007) 15 (7): 1867-1874.
Matsumoto et al., "Ingested Delphinidin-3-rutinoside Is Primarily Excreted to Urine as the Intact Form and to Bile as the Methylated Form in Rats" J. Agri Food Chem. (2006) 54: 578-582.
Park et al., "Intra-articular injection of a nutritive mixture solution protects articular cartilage from osteoarthritic progression induced by anterior cruciate ligament transection in mature rabbits: a randomized controlled trial" Arthritis and Research Therapy (2007)9:R8, 9 pages online at htpp://arthritis-research/content/9/1/R8.

(Continued)

*Primary Examiner* — Susan M Hanley
(74) *Attorney, Agent, or Firm* — Brinks Gilson & Lione; Ryan L. Marshall; Bryan Richardson

(57) ABSTRACT

Methods of treating an arthritic joint of a subject, including administering a pharmaceutical composition by injection into the arthritic joint, wherein the composition includes an anthocyanin or anthocyanidin, glucose, and a pharmaceutically acceptable carrier.

20 Claims, 17 Drawing Sheets

(56) References Cited

OTHER PUBLICATIONS

Reeves et al., "Recurrent Dislocation of Total Knee Prostheses in a Large Patient: Case Report of Dextrose Proliferant Use" Arch. Phys. Med. Rehabili. (1997) 78: 1039 Poster 35.
Reeves et al., "Randomized Prospective Double Blind Placebo-Controlled Study of Dextrose Prolotherapy for Knee Osteoarthritis with our without activity" Alternative Therapies (2000) 6(2): 68-80.
Reddy et al., "Relative Inhibition of Llpid Preoxidation, Cyclooxygenase Enzymes, and Human Tumor Cell Proliferation by Natural Food Colors" J. Agri. Food Chem (2005) 53: 9268-9273.
Seeram et al., "Cyclooxygenase inhibitory and antioxidant cyanidin glycosides in cherries and berries" (2001) 5(5):362-369.
Thakkar et. al., "Efficacy of chitosan microspheres for controlled intra-articular delivery of celecoxib in inflamed joints" J. Pharmacy Pharmacology (2004) 56: 1091-1099.
The six types of synovial joints from http://www.ask.com/question/sixt-types-of-synovial-joints, downloaded Feb. 20, 2014.
Thucker, M. "Lidocaine Contact Allergy Increasing with Topical Use" (2007) from http://www.acept/Content.aspx?id=26848, downloaded Jul. 10, 2014.
Matsumoto et al., Journal of Clinical Endocrinology and Metabolism 1996; 81:150-5.
Abelson et al, "The Other Side of Antibiotics", Review of Ophthalmology ,Online Publication, Jun. 2008 <http://www.revophth.com/content/d/therapeutic.sub.--topics/i/1227/c/2-3088/>.
Ahmed et al., ECAM 2005; 2:301-8.
Anderson et al., J Agric Food Chem, 2004; 52(1):65-70.
Baeurle et al., Polymer 2009; 50:1805-13.
Barbero et al., OsteoArthritis and Cartilage, 2004;12:476-84.
Bernardeau et al., Ann. Rheum. Dis., 2001; 60(5):518-20.
Buckwalter et al., J. Bone Joint Surg. Am., Apr. 1997; 79:612-32.
Bulstra et al., "The Effect In Vitro of Irrigating Solutions on Intact Rat Articular Cartilage", The Journal of Bone and Joint Surgery [BR], vol. 76-B 1994, p. 468-470.
Cai et al., Osteoarthritis Cartilage, Sep. 2002; 10(9):692-706.
Ceuninck et al., Arthritis Res Ther 2004; 6(5):R393-R403.
Chen et al., Arthritis Research and Therapy 2008; 10:223.
De Bari et al., Arthritis and Rheumatism, Aug. 2001; 44(8):1928-1942.
Fortier et al., J Bone and Joint Surg Mar. 2002; 84-B(2): Guccione et al., American Journal of Public Health, 1994; 84(3):351-358.-288.
Frei, EurekAlert! Mar. 2007, news release by Oregon State University.
Grimberg et al., J Cell Physiol Apr. 2000; 183(1):1-9.
Grogan et al., Arthritis & Rheumatism, Feb. 2, 2007;56(2)586-95.
Guccione et al., American Journal of Public Health, 1994; 84(3):351-358.
He et al. Zhongguo Zhong Yao Za Zhi (2005): 1602-5 English (abstract only) downloaded from PubMed on Mar. 11, 2011.
He et al. Zhongguo Zhong Yao Za Zhi (2005): 1602-5 provided by FLS, Inc. Oct. 2011, English translation of the full paper.
Homandberg et al., Biochimica et Biophysica Acta 1996; 1317(2):143-8.
Hunziker et al., J Bone Surg [Am] 1996; 78(5):721-733.
Karlsson et al., Arthritis Research and Therapy 2009; 11:121.
Kassirer, New England Journal of Medicine Sep. 1998; 339(12):839-41.
Kay et al., Br J Nutr Jun. 2004; 91(6):933-42.
Kellner et al., J Drug Target, 2001; 9(6):439-48.
Key et al., J Bone Joint Surg Am 1925; 7:793-813.
Keyszer et al., J. Rheumatol. Feb. 1995; 22(2):271-81.
Kim et al., J Korean Acad Rehabil Med Apr. 2006; 30(2)173-178.
Ledhingham et al., Annals of Rheumatic Disease, 1993; 52:520-526.
Lis et al., Chir Narzadow Ruchu Ortop Pol., 2005; 70(6):407-10.
Lotito et al., Free Radic. Biol. Med., 2006; 41(12):1727-46.
Luo, L., et al., "Protocatechuic acid benefits proliferation and phenotypic maintenance of rabbit articular chondrocytes: An in vitro study," Experimental and Therapeutic Medicine, 9:1865-1870 (2015).
Miller et al., BMC Complimentary and Alternative Med 2006; 6:13.
Miller et al., Journal of Inflammation 2007; 4:16.
Nair et al., J Agric Food Chem, Jan. 12, 2005; 53(1):28-31.
Nakajima-Nagata et al., Biochem. Biophys. Res. Commun., 2004; 318:625-630.
Nih, Vitamin E Fact Sheet, May 2009.
O'Driscoll, Journal of Bone and Joint Surgery, 1998; 80:1795-1812.
Olsson et al., Ann Rheum Dis 2001;60:233-236.
Reagan et al., "Irrigating Solutions for Arthroscopy", The Journal of Bone and Joint Surgery, vol. 65-A, No. 5 Jun. 1983, p. 629-631.
Reeves et al., Alt Ther Hlth Med 2000; 6(2):37-46.
Reeves et al., Alt Ther Hlth Med May-Jun. 2003; 9(3):58-62.
Reeves, J Altern Complement Med. Aug. 2000; 6(4):311-20.
Schmidt et al., Osteoarthitis Cartilage, May 2006; 14(5):403-12.
Schneiderman et al., Arch Biochem Biophys Dec. 1995; 324(1):173-88.
Smith et al., British Medical Journal, 2000; 321:847-48.
Strauss et al., American Journal of Sports Medicine, Aug. 2009; 37(8):1636-1644.
Uitterlinden et al., BMC Musculoskeletal Disorders 2008; 9:120.
Wang et al., J. Agric. Food Chem. 1997,45:304-9.
Woodward et al., J. Agric. Food Chem. 2009; 57:5271-78.
Lende, Amol B., et al., "Anti-inflammatory and analgesic activity of protocatechuic acid in rats and mice," *Inflammopharmacol.*, 19:255-263 (2011).

* cited by examiner

COMPOSITIONS INCLUDING ANTHOCYANIN OR ANTHOCYANIDIN FOR THE PREVENTION OR TREATMENT OF ARTICULAR CARTILAGE-ASSOCIATED CONDITIONS

CROSS-REFERENCE TO RELATED APPLICATIONS

This application is a continuation of U.S. application Ser. No. 13/568,651 filed Aug. 7, 2012, now patented as U.S. Pat. No. 9,486,468 issued on Nov. 8, 2016, which in turn is a continuation of U.S. application Ser. No. 12/651,415, filed on Dec. 31, 2009, now patented as U.S. Pat. No. 8,263,069 issued on Sep. 11, 2012, which in turn claims priority to U.S. Provisional Application No. 61/142,070, filed on Dec. 31, 2008. The disclosures of the prior applications are hereby incorporated by reference in their entirety.

TECHNICAL FIELD

The present invention relates generally to methods and compositions for the treatment cartilage associated disorders in a subject by administering a composition which provides chondronutritive, chondroprotective, chondroreparative and chondrorestorative activity and more specifically to methods and compositions including the administration of an anthocyanin or an anthocyanidin combined with a saccharide for the prevention or treatment of articular cartilage loss in a subject.

BACKGROUND OF THE INVENTION

Osteoarthritis (OA) affects nearly 27 million Americans and poses significant costs on both the patient's health and finances. For instance, researchers found that in a study of 84,647 adult women and 70,590 adult men with health insurance, due to a higher rate of OA, women had higher annual insurer health care costs than men ($4,833 vs. $4,036) and higher out-of-pocket expenditures ($1,379 vs. $694) and thus accounted for $118 billion of the total $186 billion increase in health care expenditures. Kotlarz et al., Arthritis Rheum. 2009; 60(12):3546-3553.

Causes of OA vary, but include aging joints, genetic predisposition, previous injuries and obesity. Symptoms of OA include joint pain, swelling, stiffness, loss of motion, diminution of activities of daily living, disability and loss of work. For example, patients with knee OA report knee pain and difficulty with walking, stair-climbing and housekeeping. Guccione et al., American Journal of Public Health, 1994; 84:351-358. Osteoarthritis may affect any joint, including the hand, wrist, neck, back, knee and hip. The knee is the most common lower limb site for OA, with the disease affecting the tibiofemoral and patellofemoral joints either in isolation or combination, with the medial tibiofemoral compartment as the most commonly affected. Ledingham et al., Annals of Rheumatic Disease 1993; 52:520-526.

The microscopic changes of OA typically begin with a disruption of the surface layer of cartilage, called the superficial zone. Functionally, of the four layers of cartilage present in joints, this is the most important. In non-diseased joints the cartilage surface is smooth, enabling joint surfaces to interact without friction, due in part to the molecule lubricin. However, the cartilage of the superficial zone begins to deteriorate as OA progresses triggering an irreversible process that eventually leads to the loss of underlying layers of cartilage. The integrity of the cartilage breaks down resulting in fragments of cartilage being dispersed in the joint causing reaction of the joint lining, inflammation and the symptoms of pain and swelling. Over time, exposed bone surfaces begin to grind painfully against one another. In addition there are architectural changes in the geometry of the adjacent bone resulting in deformity, instability, angulation and loss of motion.

Conventional thought is that articular cartilage in synovial joints has little or no potential for repair or restoration following injury or disease. Buckwalter J A, Mankin N J. Instructional Course Lectures, The American Academy of Orthopaedic Surgeons (AAOS)-Articular Cartilage. Part II: Degeneration and Osteoarthrosis, Repair, Regeneration, and Transplantation. J. Bone Joint Surg. Am., April 1997; 79: 612-32. The primary reason is that, unlike other tissues, it has no innate blood supply. Instead, it is a relative acellular tissue formed primarily of a matrix of water held in place with a network of mucopolysaccharides, which themselves are glucosamines made up in part of glucose molecules.

Management strategies for OA can be regarded as primary (reducing risk factors to lessen disease incidence); secondary (intervening to slow or prevent progression to serious disease); or tertiary (treating pain and disability). Dieppe et al., Rheum. Dis. Clin. N. Am. 2003; 29(4):687716. To date, most knee OA research has focused on tertiary strategies relating to pain management. Among these strategies, the primary emphasis has been on drug therapies, which typically include unwanted side effects and can be costly. Dieppe et al., BMJ 2004; 329(7471):867-868.

Non-operative treatment depends on the joint but often includes medication and exercise. For instance, OA patients are often treated with nonsteriodal anti-inflammatory drugs (NSAIDs) such as MOTRIN and CELEBREX. Alternatively, patients may be treated with the steroid hormone Cortisone, often by injection, which reduces inflammation by suppressing the immune system.

Viscosupplementation with hyaluronic acid (HA) is gaining popularity in the nonoperative management of OA. HA is believed by some to have anti-inflammatory, anabolic and chondroprotective actions thereby reducing pain and improving patient function. Strauss et al., American Journal of Sports Medicine, 2009 August; 37(8):1636-1644. However, others report that within hours of intra-articular administration, aseptic acute arthritis develops, which may be caused by pro-inflammatory HA degradation products. Bernardeau et al., Ann Rheum Dis 2001; 60:518-20. A French study considered that a single HA injection may not have much effect on the knee because it may be rapidly cleared from the synovial fluid compartment. Thus, the research regarding the use of HA appears inconsistent; however, while HA may eventually prove to be useful, intra-articular injection of exogenous HA still remains a significant concern. For completeness, the AAOS 2008 guideline publication on non-arthroplasty treatment did not recommended for or against the intra-articular administration of HA.

Administration of chondroitin sulfate is also considered a potential candidate for treatment. Chondroitin sulfate is a sulfated gycosaminoglycan (GAG) composed of alternating sugars of N-acetyl galactosamine and glucuronic acid. It is an important structural component of cartilage and provides much of its resistance to compression. Baeurle et al, Polymer 2009; 50:1805-13. The AAOS 2008 guideline publication did not recommend the use of chondroitin sulfate. The AHRQ report stated that "the best available evidence found that glucosamine hydrochloride, chondroitin sulfate, or their combination did not have any clinical benefit in patients with primary OA of the knee."

As the name implies, alternative medicine provides alternatives to conventional medical treatment or management of OA. It has been said that "[w]hat most sets alternative medicine apart, in our view, is that it has not been scientifically tested and its advocates largely deny the need for such testing." Kassirer, New England Journal of Medicine 1998 September; 339(12)839-41. Since many therapies lack scientific studies, typically the AAOS does not recommend for or against such treatments.

Among the alternative medicine approaches, one of particular interest is the use of "nutraceuticals." Nutraceutical, a term combining the words "nutrition" and "pharmaceutical," was originally defined by Dr. Stephen L. DeFelice to describe a nutritional product that claims to provide medicinal benefits in addition to their regular nutritional value. Nutraceuticals is a broad term, which can refer to foods, dietary supplements, medical foods and functional foods that may provide prevention and treatment of illness or disease. Importantly, nutraceutical foods are not subject to the same testing and regulations as pharmaceutical drugs. However, nutraceuticals have become increasingly mainstream and can be considered a dietary approach or nutritional approach since the extracts or foods are typically orally ingested.

Nutraceuticals for most part are extracts of botanicals. They are mixture of various materials, some known and other unknown. Thus, the knowledge of their metabolism is often unknown. They are described as belonging to various chemical groups, which in order of progression from general to specific are as follows, with each successive being a sub group. In fact, the absence of testing and scientific standards tend to confuse consumers and the scientific community as to what the mixtures actually are, their activity and biological effect.

Among the common nutraceuticals are antioxidants, in particular Vitamin C and E. The pharmacophore of vitamin C is ascorbate ion and is required for a range of essential metabolic reactions in animals. Ascorbate ion protects the body against oxidative stress and is cofactor in several vial enzymatic reactions. Vitamin E is a fat-soluble antioxidant that stops the production of reactive oxygen species formed when fat undergoes oxidation. NTH, Vitamin E Fact Sheet, 2009 May. Each are recommended for a wide variety of medical conditions even without scientific basis.

In recent years the poly phenols have been popularized, including anthocyanins and anthocyanidins. Attention has been drawn to their potential to benefit articular cartilage nutrition. Experiments with direct application of such products to articular cartilage and cells have shown they enhance the growth hormone production within the cartilage and have an antioxidant effect. One such report was that of Miller et al. Prograde, which is an extract enriched for long chain proanthocyanin oligomers, was reported to have a promising safety profile, significant chondroprotective and antioxidant actions, directly inhibit MMP activity and promote the production of cartilage repair factor, insulin-like growth factor-1 (IGF-1), in explants and cell culture which suggested it may offer therapeutic benefits in joint health, wound healing and inflammation. Miller et al., Journal of Inflammation, 2007; 4:16. However, Miller acknowledges that repair and cartilage growth was not measured. Thus, while promising in vitro, the results did not transfer to desired activity in vivo. Closer inspection of Miller's report reveals there is little characterization of the ingredients. That is, the extracts are not synthesized, pharmaceutically pure or well characterized ingredients, but instead includes a collection of unknowns suspected of including oligomers referred to as proanthocyanins. That is, it appears the compounds in Miller are considered to be oligomeric chains or long polymer chains; however, the chains themselves are not well defined. Consistent with unknown extracts or elixers, Prograde is provided as a nutraceutical and is thus exempt from characterization necessary to understand relevant structures or ingredients. This is consistent with its labeling as a dietary or nutritional supplement, which further confuses the matter. Accordingly, it is not in fact clear what the active ingredients may be in Prograde, if any. That is, while Miller provides an extract believed to be enriched in proanthocyanin oligomers, the ingredients themselves, including the "oligomers" remain to be characterized. Nonetheless, it is an object of Miller to provide extracts for oral ingestion to deliver dietary or nutritional supplemental ingredients to their intended target.

In fact, the assumption that the oral intake of food or extracts of food would reach the articular cartilage in the synovial joint has not been supported by any evidence. The marketing of nutraceuticals is not under FDA control and therefore may make claims accompanied by "disclaimers" of the benefits to articular cartilage. The evidence from the nutrition literature would indicate the likelihood of ingested food or extracts reaching the synovial joint is remote. That is, the lack of desired in vivo activity in the Miller et al. experiment appears consistent with the literature regarding the metabolism of flavonoids in the body. In 2007 it was found that inside the body, flavonoids themselves are of little or no direct antioxidant value. Lotito et al., Free Radic. Biol. Med. 41(12)1727-46. Body conditions proved to be unlike controlled test tube conditions, and the flavonoids were found to be poorly adsorbed (less than 5%), with most of what is absorbed being quickly metabolized and excreted. It has been theorized that increase in antioxidant capacity of blood seen after consumption of flavonoid-rich foods is not caused directly by the flavonoids themselves, but due to increased uric acid levels that result from expelling flavonoids from the body. Frei, EurekAlert! 2007 March, news release by Oregon State University. According to Frei, large doses of dietary supplements might do no additional good over a relatively modest intake since the body sees them as foreign compounds and modifies them for rapid excretion in the urine and bile. Based on Frei's findings, flavonoids appeared to have 3-5 times more antioxidant capacity than vitamins C or E but since flavonoids were poorly absorbed in the body (less than about 5%) vitamin C accumulated more in cells where it is 1,000 to 3,000 times more active as an antioxidant.

The lack of in vivo activity in the Miller et al. study is also consistent with the half-life of flavonoids. For instance, the anthocyanin cyanidin-3-glycoside has a half-life of about 90-120 minutes. This may be due in part to the surrounding acidic pH, which is substantially different than the approximate neutral pH of the bloodstream. As such, these compounds would not be predicted to cross biological barriers to affect the cartilage. Thus, considerations of flavonoids for potential treatments must account for their in vivo challenges from oral ingestion to end target tissue.

By way of contrast, a pharmaceutical is a well-defined substance. It is usually a single molecule, occasionally a compound, and most often not in oligomeric chains. They are closely regulated by the FDA. The foundation for their efficacy and safety are a necessity. Their use in clinical practice require more rigorous testing prior to market approval as with various phases of clinical trials. Pharmaceuticals are administered by gastrointestinal route and/or bodily injection. After FDA approval, the process of oversight continues. This is in stark contrast to the less demanding foundation or process for marketing a nutraceutical.

Therefore, if in fact these polyphenols are a benefit to the articular cartilage, there is a need to consider the efficacy and safety of the direct application by injection. There is a need for such a novel method and specific substances that are not a food extract of a mixture of molecules known and often unknown, but molecules or compounds of pharmacological composition and purity to achieve a therapeutic benefit to articular cartilage.

Glucose is a building block of many tissues including cartilage, where the main product produced by the cartilage cell are mucopolysaccharides, which form a network of matrices that hold a high percentage of water. Thus, some believe glucose itself may be a potential candidate for the treatment of arthritic conditions. For instance, dextrose injections in the knee and base of the thumb showed repair and clinical improvement from osteoarthrititis. Reeves et al, Alt Ther Hlth Med 2000; 6(2):37-46. Afterwards, a three year consecutive patient study of 10%-25% dextrose injection in patients with ACL laxity, 87% of whom had osteoarthritis, had improved tightening of the ACL and decreasing symptoms of osteoarthritis. Reeves et al., Alt Ther Hlt Med 2003 May-June; 9(3)58-62. Tissue regeneration in articular cartilage in rabbit has also been shown with 10% dextrose by injection. Kim et al., J Korean Acad Rehabil Med 2006 April; 30(2):173-178. Though studied alone, it has also been proposed to use a combined therapy with glucose. However, when coupled with amino acids, injection of 10% dextrose showed no measurable improvement compared to 10% dextrose alone. Park et al., Arthritis Research and Therapy, 2007; 9(1):R8.

Glucose is an attractive candidate since it is ever present in all body tissues as well as synovial joints, including the synovium, the synovial fluid and cartilage; however, glucose levels in the synovial fluid are less than those in the blood. It may be that increasing glucose concentration stimulates human ostearthritic synovium to make hyaluronic acid (HA). The addition of 5 mM glucosamine increased HA production approximately 2-fold in osteoarthritic synovium explants but 0.5 mM glucosamine did not. Uitterlinden et al., BMC Muscoskeletal Disorders 2008:9;120. Thus, it appears physiologic levels of glucose may be insufficient for stimulating HA production.

Further, although glucose has been shown to provide an anabolic effect on cartilage it does not have a chondroprotective effect. That is, while cartilage can be formed, its formation merely mitigates its loss.

Insulin-like growth factor-1 (IGF-1) is also considered to be a potentially viable treatment for cartilage conditions. It has been known for years that IGF-1 is chondroreparative. IGF-1 is believed to play a key role in cartilage homeostasis, balancing proteoglycan synthesis and breakdown. Schmidt et al., Osteoarthritis Cartilage, 2006 May; 14(5):403-12. The action of IGF-1 on chondrocytes is mediated through the IGF-1 receptor. Taylor et al., FEBS Lett. 1988; 236:33-8. Composites of chondrocytes and polymerized fibrin were supplemented with IGF-1 during arthroscopic repair of full-thickness defects in horses and were shown to improve the repair capabilities of chondrocyte-fibrin grafts. Fortier et al., J Bone and Joint Surg 2002 March; 84-B(2)276-288. Although IGF-1 is naturally present in the synovium (see Keyszer et al., J. Rheumatol. 1995 February; 22(2)271-81), the total IGF-1 in normal human synovial fluid is an order of magnitude lower than that in the serum. Schneiderman et al., Arch Biochem Biophys 1995 December; 324(1):173-88. However, IGF- has been shown to be elevated in the synovial fluid of patients with osteoarthritis, in contrast to decreased levels of IGF-II and neutral levels of IGFBP-3. Matsumoto et al., Journal of Clinical Endocrinology and Metabolism 1996; 81:150-5. Increased IGF-1 production by human osteoarthritic chondrocytes is not dependent on growth hormone action. Dore et al., Arthritis and Rheutism, 1995; 38(3):413-419. Thus, effective stimulation of IGF-1 may require additional experimentation.

While IGF-1 is believed to increase cartilage production, exogenous administration of IGF-1 as well as human growth hormone (HGH) possess risks to patient health. Although IGF-1 is believed to enhance proliferation of cells and thus may also enhance proliferation of chondrocytes, it is believed to do so by inhibiting apoptosis, which includes apoptosis of cancer cells. Smith et al., British Medical Journal, 2000; 321:847-48. In fact, many studies have implicated IGF-1 in carcinogenesis. See Grmberg et al., J Cell Physiol 200 April; 183(1):1-9.

Insulin is known to bind to the IGF-1 receptor and to illicit significant responses in cartilage. Kellner et al., J Drug Target, 201; 9(6):439-8. Thus, insulin may also be a promising approach for cartilage healing. Administration of a slow release formulation of insulin was provide to cartilaginous explants, which resulted in the stimulation of proteoglycan (PG) synthesis, inhibition of PG release and nitric oxide production and overcame detrimental effects of interleukin-1(IL-1). Cai et al., Osteoarthritis Cartilage, 2002 September; 10(9):692-706. At one time it was believed that only the islet cells of the pancreas would produce insulin; however, many other cells are known to produce insulin under certain conditions. Adult stem cells from the intestine have been converted into insulin-producing beta cells in the pancreas of diabetic mice. Suzuki, PNAS 10.1073/pnas.0936260100. Stem cells extracted from the spleen can change into insulin-producing pancreatic islet cells. Fasutman et al, Science 2003 November; 302; 1123-1127. Bone marrow stem cells transplanted into the pancreas can morph into insulin-producing beta cells. Mehbood et al., Journal of Clin. Investig. 2003 March; 111(6). Adult hepatic progenitor cells can be induced into insulin-producing cells. Nagata et al., Biochem. Byophys. Res. Commun. 318:625-630. Thus, the production of insulin may be approached using a variety of cell types found throughout the body given the proper environment.

Joint replacement is the only established treatment for end-stage OA. In the case of the knee, the cost for such an operation is high—an estimated $35,000 for those without health insurance and the operation also typically entails a 3-7 day hospital stay. During the surgery the doctor assesses the condition of the joint surfaces, removes damaged bone and cartilage, and implants new joint surfaces made of plastic and metal. These new joint surfaces are not permanent, and will likely need to be replaced after 10 to 15 years. Alternative surgical procedures can include debridement procedures, which include arthroscopic procedures for mechanical problems and loose bodies; and osteotomy, which is a procedure to alter the forces across the joint.

While conventional thought is that articular cartilage has no potential for repair, studies are currently underway to explore the use of the synovium, which is the soft tissue that lines the non-cartilaginous surfaces. The synovium is believed to have regenerative capabilities. The surgical removal of the synovium of laboratory rabbits resulted in regeneration of the synovium to prior status in 6 weeks. Key et al, J Bone Joint Surg Am 1925; 7:793-813. The same is true in humans. Ostergaard et al, Ann Rheum Dis 2001; 60:233-236.

One such proposed treatment involves the use of synovium explants. U.S. Pat. No. 7,575,743 by Hunziker proposes using an excised sheet of synovial membrane as an explant for the treatment of a shallow cartilage defect. More specifically, synovial cells are harvested from the synovial membrane, cultured, then used to fill a cartilage defect together with a transforming factor. The theory behind this procedure is that synovium adjacent to the articular cartilage reflection will migrate and heal cartilage lesions in the immediate proximity of the reflection, but not those remote to the intact synovium. Hunziker et al., J Bone Surg [Am] 1996; 78-A; 721-733. Thus, use of synovium tissue treated in this manner may prove useful.

In a more elegant procedure, US Patent Publication 2006/0051327 by Johnson proposes a treatment including the removal of synovial villi from the synovial capsule and its use as an explant. The synovial villi are the finger-like projections that exist in some instances of joint injury and/or disease. These villi are known to house red blood cells, white blood cells as well as plasma with circulating electrolytes, growth hormones, and circulating insulin. In addition the synovial villi have increased number of synovial cells in depth and extended surface area. There are also mesenchymal stem cells (MSC). As such, stem cells and other beneficial components found within the villi, if transferred, would assist in repair while portions of the synovium, which remain, are permitted to rebuild the synovial membrane at the site of harvest in furtherance of Key et al. In addition, there are primary repair cells, fibroblasts and angioblasts, which may also contribute to repair of cartilage.

Although synovium explants have been demonstrated to heal damaged cartilage, the methods still require surgical processes, which can be expensive and provide additional health risks. Accordingly, there remains a need to develop compositions that stimulate or enhance the production of articular cartilage and that reduce or eliminate the need for surgical intervention or that increase the rate of healing from surgery.

Thus, while numerous approaches for the treatment of OA conditions have been proposed, there remains a need to provide improved therapies that address the biological activity of the molecule as well as the potential innate barriers the body possesses against delivery to the affected joint.

SUMMARY OF THE INVENTION

The present invention addresses the need to develop compositions and methods for the repair or regeneration of cartilage. Specifically, the present invention provides methods and compositions that stimulate or induce cartilage repair or regeneration while protecting against cell death or degradation of cartilage. Further, the invention provides methods and formulation that deliver chondronutritive and chondrorestorative activities to the affected joint. Still further, the methods and compositions address the challenges faced with delivery of the desired composition to the affected joint or region. Thus, the present invention provides a compositions and methods may be used to treat a variety of cartilage disorders or cartilage-associated medical conditions.

In one aspect of the present invention, a pharmaceutical composition for repair or regeneration of cartilage is provided, including a) an anthocyanin or anthocyanidin; b) glucose; and c) a pharmaceutically acceptable carrier. Among the anthocyanins include cyanidin-3-glucosidase or delphinidin-3-glucosidase, cyanidin-3-galactosidase, and pelargonidin-3-galactosidase. Among the anthocyanidins include cyanidin, delphinidin, pelargonidin, malvidin and petunidin. In some embodiments the anthocyanidin is provided less than 200 uM and in other embodiments about 100 uM. In some embodiments, glucose is provided in about 0.5% to about 10%.

In another aspect of the present invention a method of treating an arthritic joint of a subject is provided, which includes administering the pharmaceutical composition by injection into the arthritic joint. In some embodiments, the composition is provided in a biodegradable microsphere or a slow release bioadsorbable material, such as 50/50 D, L lactide/glycolide or 85/15 D, L lactide/glycolide.

In another aspect of the present invention a method of treating an arthritic joint in a subject is provided, which includes excising synovial villi from a synovial capsule of a joint; culturing the synovial villi with a composition comprising an anthocyanin or anthocyanidin and optionally glucose; and introducing the cultured synovial villi to the arthritic joint. The synovial villi may be excised by selective excision of linger-like projections from an underlying synovial capsule.

In a related aspect, the method includes excising synovial villi from a synovial capsule of a joint to provide an explant; introducing the explant to the arthritic joint; and administering a composition intra-articularly to the arthritic joint, wherein the composition comprises anthocyanin or anthocyanidin, and optionally glucose.

In another aspect of the present invention a method of treating an arthritic joint is provided, which includes harvesting mesenchymal stem cells from the synovium; culturing the stem cells with a composition comprising an anthocyanin or anthocyanidin; and optionally glucose; and introducing the cultured stern cells to the arthritic joint.

In another aspect of the present invention a method for increasing expression of IGF-1 in a cartilage explant is provided, which includes providing a cartilage explant from a patient suffering from osteoarthritis and administering to the explant a composition including an anthocyanin or anthocyanidin and glucose. The explant may be introduced into the site suffering from osteoarthritis.

In another aspect of the present invention a method of saturating insulin growth factor binding protein (IGFBP) in an arthritic joint is provided, which includes intra-articularly administering to the arthritic joint a composition that stimulates production of IGF-1 in the joint in an amount sufficient to saturate the IGFBP, wherein the composition is an anthocyanin or anthocyanidin, and optionally glucose. The IGF-1 may be produced by the synovium in the joint and may be produced by increasing IGF-1 gene expression.

In another aspect of the present invention a method for treating damaged cartilage is provided, which includes administering a composition which comprises a monosaccharide covalently linked to a non-toxic base molecule to the cartilage, wherein the compound stimulates regeneration of the damaged cartilage. The composition may be an anthocyanin or anthocyanidin and may stimulate IGF-1 in the joint to regenerate the damaged cartilage. The composition may be administered with IGF-1, insulin or a mixture thereof. The composition may be provided in microspheres of slow release bioadsorbable material, such as 50/50 D, L lactide/glycolide or 85/15 D, L lactide/glycolide.

In another aspect of the present invention a method of treating damaged cartilage in an affected joint is provided, which includes stimulating the production of IGF-1 by the synovium or synovial cells through the intra-articular administration of a composition, wherein the composition also prevents the degradation of cartilage, such as through antioxidant properties. The composition may include an anthocyanin or an anthocyanidin and glucose.

In another aspect of the present invention, a method of modulating the production of IGF-1 in the synovium of a joint suffering from a cartilage-associated disorder is provided, which includes the intra-articular or juxta-articular administration of an anthocyanin or anthocyanidin and glucose.

DETAILED DESCRIPTION OF THE INVENTION

Figure 1:
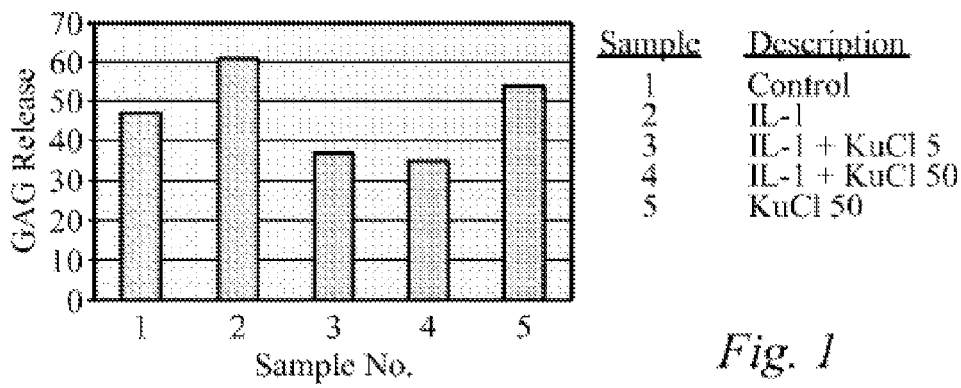
FIG. 1 depicts a chart summarizing GAG release data measured from human explant cultures as described in Example 1 for kuromanin Sample 1 provides the control. Sample 2 was treated with IL-1 alone, which induces degradation of cartilage. Sample 3 was treated with IL-1 and kuromanin (KuCl) at 5 ug/mL. Sample 4 was treated with IL-1 and KuCl at 50 ug/mL. Sample 5 was treated with KuCl at 50 ug/mL. In summary, KuCl blocked IL-1 induced GAG release.

As an introduction, the present invention provides methods, composition and uses for treating or preventing various cartilage-associated disorders or injuries. In particular, the present invention provides methods and compositions for the prevention or treatment of cartilage-associated conditions or disorders of the hand, foot, ankle, knee. hip, spine, growth plates, intervertebral disc and the like, and is particularly useful as treatment of cartilage disorders or cartilage-associated medical conditions such as arthritis, and more particularly traumatic and osteoarthritis. Conditions such as lupus and rheumatoid arthritis may also benefit from such treatment as will genetic or post-surgical conditions that result in damaged cartilage.

Preferably, the methods and compositions are used for the treatment of humans. However, the methods and compositions are also useful in the veterinary arts, such as for the treatment of animals and in particular mammals. A variety of cartilage-associated disorders are prevalent in mammals, including in *equine* or horse and *canis* or dog. As such, the methods and compositions will also be useful for the treatment of a variety of mammals, including horses, dogs, cats, livestock, humans and the like.

The methods and compositions provided herein include an anthocyanin or anthocyanidin and preferably glucose. Most preferably, the composition is provided in a pharmaceutically acceptable carrier suitable for the particular administration, which is preferably intra-articular injection.

Anthocyanins and anthocyanidins are demonstrated herein to provide chondroprotective and chondronutritive activities, which may be transferred directly to a joint or joint capsule suffering from a cartilage-associated condition or injury. These beneficial activities correlate with the ability of the anthocyanin and anthocyanidin to modulate the synovium, thereby increasing both IGF-1 gene expression and IGF-1 production. Though nonlimiting, increasing the availability of IGF-1 within the affected joint capsule is believed to counter soluble IGF-1 binding proteins in the affected region, and thus increase its availability for binding to receptor in or at the cartilage cell. IGF-1 is thus permitted to interact with cartilage cells to produce mucoplysaccharides for chondronutritive activity and chondrorepair and/or chondrorestoration. Further, by simulating the body's innate production of IGF-1 the present invention enhances the body's natural protective mechanism while avoiding potential adverse effects associated with administration of exogenous IGF-1 or human growth hormone (HGH). Still further, the rapid breakdown of the anthocyanin or anthocyanidin itself permits improved regulation of IGF-1 gene expression and production while ensuring its removal and thus eliminating potential downstream effects on other potential regulatory pathways. As such, the compositions and methods provide both efficacy and safety.

Benefits derived from anthocyanins/anthocyanidins may also be due in part to their antioxidant activities. For instance, the scavenging of free radicals within the synovial fluid may prevent attack on cartilage, thereby providing chondroprotection.

When combined with glucose, the anthocyanins and anthocyanidins are also shown to significantly improve the production of cartilage. As such, when combined with glucose the composition further enhances chondroreparative and chondrorestoratative activity. Stimulation of new cartilage may occur, in part, by increasing gene expression and production of IGF-1 as well as providing substrate for glucosamine in the building of the cartilage matrix.

While these compositions and methods alone will provide an effective therapy for the treatment of cartilage associated disorders, when used in combination with alternative therapies treatment may be further enhanced.

In one exemplary method administration of the composition is combined with the use of an explant of synovial villi. In such embodiments the synovial villi may be harvested from a subject, cultured in the presence of the composition and introduced to the site of injury. In alternative embodiments the synovial villi may be provided as an explant, introduced at the site of injury then followed by one or more intra-articular injections of the composition.

As will become apparent to one skilled in the art, administration of the composition may be combined with a variety of surgical or nonsurgical procedures to enhance treatment over the procedures alone.

Definitions

Unless expressly defined otherwise, all technical and scientific terms used herein have the same meaning as is commonly understood by one of ordinary skill in the art to which this invention belongs. All publications referred to throughout the disclosure are incorporated by reference in their entirety. In the event there exists a plurality of definitions or meanings for a term, the interpretation is to be construed consistent with this section and the spirit and scope of this document as a whole.

The term "cartilage disorder" or "cartilage-associated disorder" as used herein refers to a medical condition that includes as a characteristic, reduced or damaged cartilage as compared to a control or normal subject. A cartilage disorder may result from disease, injury and the like. A cartilage disorder may be a genetic condition or a viral condition. A cartilage disorder also includes secondary injuries to the joint such as those found in medical conditions such as gout. The cartilage disorder also includes systemic diseases with secondary joint conditions, such as lupus and rheumatoid arthritis. The cartilage disorder may be an injury that results in damaged and/or reduced cartilage. The cartilage-associated disorder may be osteoarthritis.

The term "chondroprotective" or "chondroprotective agent" as used herein refers to a process, substance or molecule that inhibits or reduces the degradation of cartilage or chondrocytes. Chondroprotection may occur by decreasing of apoptosis and may be an anti-apoptotic agent. Chondroprotection protects cartilage from effects of IL-1 in vitro. A chondroprotective agent may be identified by assessing whether the compound prevents induced degradation of cartilage or chondrocytes. A chondroprotective agent may be identified from identifying known antioxidant properties. TGF-β, IGF-1 and anthocyanins/anthocyanidins are chondroprotective. Some surgical procedures, such as autogenous bone grafting are chondroreparative. Orthosis, such as through the use of unloader braces or some insoles, may be chondroprotective.

The term "chondronutritive" or "chondronutritive agent" as used herein refers to a process, substance or molecule that activates a cartilage cell to produce or enhances the production of glucopolysaccharides.

The term "chondroreparative" or "chondroreparative agent" as used herein refers to a process, substance or molecule that causes cartilage to repair, such as with fibrocartilage. Surgical procedures such as abrasion arthroplasty, microfracture, autogenous osteochondral grafting and joint unloading by ostetomy are considered chondroreparative. Orthosis, such as through the use of unloader braces or some insoles, may be chondroreparative.

The term "chondrorestorative agent" as used herein refers to a process, substance or molecule that causes cartilage to be restored to its normal hyaline pattern or nature. A chondrorestorative agent restores or improves normal activities or functions to the cartilage. The term "pharmaceutically acceptable carrier" as used herein refers to the acceptance or use of the carrier in the pharmaceutical industry. Preferably the carrier is approved by the Federal Drug Administration (FDA) for use in humans. Exemplary carriers include physiological solutions including but not limited to glucose, dextrose, normal saline, phosphate buffered saline (PBS) or Ringer's solution.

The term "therapeutically effective amount" as used herein refers to an amount of an active ingredient that produces the intended result.

The term "proximate" or "proximate to" as used herein refers to a location that is sufficiently near in location that the intended effect or result occurs. For example, synovium explants proximate to damaged cartilage are able to migrate and affect repair. Injections or infusions proximate to damaged cartilage deliver pharmaceutical composition to damaged cartilage.

The term "alkyl" or "alkyl group" as used herein refers to a straight or branched hydrocarbon chain having from 1 to 15 carbons. Non-limiting examples include ethyl ($—CH_2CH_3$), propyl ($—CH2CH2CH_3$), butyl ($—CH2CH2CH_2CH_3$) and the like.

The term "alkoxy" or "alkoxy group" as used herein refers to a straight or branched hydrocarbon chain having from 1 to 15 carbons and linked to oxygen. Non-limiting examples include methoxy (—OCH3), ethoxy ($—OCH_2CH_3$) and the like.

The term "intra-articularly" as used herein refers to direct administration of a composition into the cavity enclosing or associated with a movable joint requiring treatment, so that substantial direct contact between the administered composition and the cartilage is achieved. The cavity may be associated with any moveable joint, including a ball and socket joint, a hinge joint, a pivot joint and a saddle joint. Such joints may be found throughout the body. Further, administration may occur into a cavity or cartilage matrix or synovial facet joint associated with the spine.

The term "juxta-articular" or "juxta-articularly" as used herein refers to the administration of a composition near an articular joint requiring treatment.

Methods of Treating Cartilage-Associated Conditions and Disorders

In one aspect of the present invention a method for the treatment of a cartilage-associated condition or disorder is provided, which includes administering to a patient in need thereof a composition including an anthocyanin or an anthocyanidin, and optionally glucose. The composition is provided with a pharmaceutically acceptable carrier.

Anthocyanins and anthocyanidins are known to have potent antioxidant activities in vitro. (see Wang et al., J. Agric. Food Chem. 1997, 45:304-9, kuromanin (cyanidin-3-glucoside) had 3.5 times the oxygen radical absorbing capacity compared to Trolox (Vitamin E)). However, transfer of antioxidant properties has not been confirmed in vivo. This is likely because, in part, flavonoids, such as anthocyanins do not effectively cross the blood/synovium barrier. For instance, flavonoids are poorly adsorbed (less than 5%) with most of what is being adsorbed being quickly metabolized and excreted. (see Frei et al. 2007). In fact, the half-life of cyanidin-3-glucoside is predicted to be about 90-120 minutes. The mechanism of flavonoid metabolism has been suggested to include their degradation into phenolic acids and aldehyde in vivo. Woodward et al., J. Agric. Food. Chem 2009; 57:5271-78. The metabolic conversion of cyanidin glycosides in human subjects has also been confirmed through analysis of urine and serum. Kay et al., Br J Nutr 2004 June; 91(6):933-42. Thus, while in vitro the antioxidant activities have been impressive, in vivo it is more useful to administer Vitamin C for antioxidant activity.

To confirm the results of Frei, Lolita et al., Woodward et al. and Kay et al., an experiment was performed to assess whether an anthocyanin could be orally delivered to an affected joint or whether it would be metabolized as predicted by the above authors. In the study, a subject suffering from OA of the knee ingested the extract chokeberry. Chokeberry includes, in comparison per 100 g FW: 37.6 mg cyanidin-3-glucoside; 51.5 cyanidin-3-xyloside; 989.7 mg cyanidin-3-galactosidase; 399.3 mg cyanidin-3-arabinoside; and 2.3 mg pelargonidin-3-arabinoside. Accordingly, chokeberry includes a high concentration of anthocyanins; greater than gooseberry, elderberry and red currant. Afterwards, both urine and synovial fluid from the affected knee joint was collected and analyzed. No trace of anthocyanin was found in the synovial fluid; however anthocyanin was found in the urine. Accordingly, it was confirmed that ingested anthocyanin does not cross the biological barriers to enter the knee. That is, there appears to be a blood-synovial barrier that is difficult to cross.

A central problem solved by the present invention is the adaptation of the composition for direct administration to the affected joint. While previous oral administration techniques were unlikely successful, such as those pursued by Miller et al., the study above supports the finding that the body treats anthocyanins and anthocyanidins as foreign bodies and rapidly metabolizes them for excretion through the urine or bile. That is, they are not permitted to traverse the body's synovial barrier, which is particularly adapted to regulate the presence and abundance of compounds, factors and proteins within the articular joint. The problem of delivery and circumventing rapid metabolism has now been solved in part by providing an alternative administration route and technique. Preferred delivery of the compositions of the present invention is through intra-articular injection where the composition can act directly and with known effective dose in the joint requiring treatment.

The potential role of anthocyanins and anthocyanidins for the treatment of cartilage-associated disorders was further evaluated to consider efficacy and safety. If a therapeutic route would be developed, both efficacy and safety would be required. We have a well-defined and identified single molecules tested that were selected and representative of the anthocyanin/anthocyanidin group. To confirm results correlated with the compositions themselves, substantially pure (greater than 97%) compounds were used to avoid variations or contaminants found in extracts.

Figure 2:
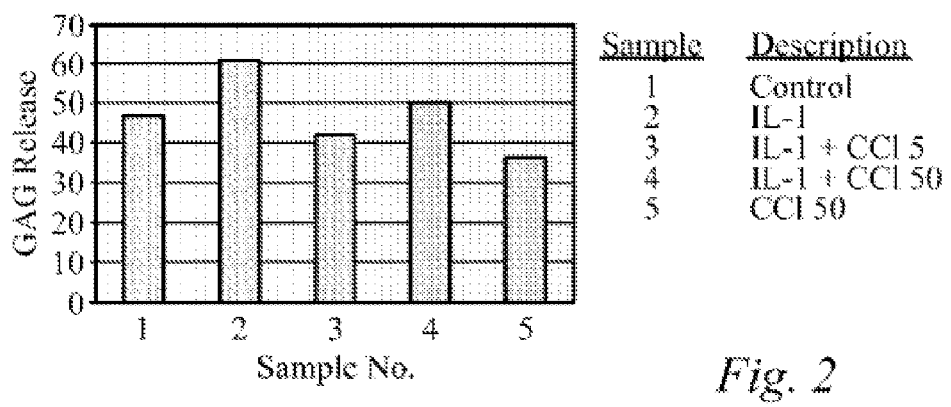
FIG. 2 depicts a chart summarizing GAG release data measured from human explant cultures as described in Example 1 for cyanidin. Sample 1 provides the control. Sample 2 was treated with IL-1 alone. Sample 3 was treated with IL-1 and cyanidin (CC1) at 5 ug/mL. Sample 4 was treated with IL-1 and CC1 at 50 ug/mL. Sample 5 was treated with CC1 at 50 ug/mL. In summary, CC1 blocked IL-1 induced GAG release.

The role of anthocyanins/anthocyanidins as chondroprotective agents was considered by culturing human cartilage explants in the presence of IL-1, which is known to induce degradation of cartilage. Referring to FIGS. 1 and 2, both kuromanin and cyanidin were able to prevent GAG (glycosaminoglycan) release compared to control. Thus, both kuromanin and cyanidin proved to be chondroprotective. The antioxidant activities of anthocyanins and anthocyanidins are believed to contribute to their chondroprotective activities. For instance, it may be that anthocyanins or anthocyanidins scavenge free radicals within the articular joint, thereby preventing attack on vulnerable cartilage.

Although it was established that both kuromanin and cyanidin were chondroprotective agents, potential mechanisms of action were also studied. In particular IGF-1 gene expression and production was assessed in cartilage explants. IGF-1 is known to exist in osteoarthritis synovium and is known to have a healing effect on articular cartilage. (Schmidt M B et al., Osteoarthritic Cartilage 2006 May; 14(5):403-12). IGF-1 is also believed to have a poor anabolic efficacy in cartilage in osteoarthritis partly because of its sequestration by abnormally high levels of extracellular IGF-binding proteins (IGFBPs). Ceuninck et al., Arthritis Res Ther 2004; 6(5):R393-R403. Accordingly, an increase in IGF-1 production could overcome the IGFBPs and potentially induce cartilage repair.

Figure 9:
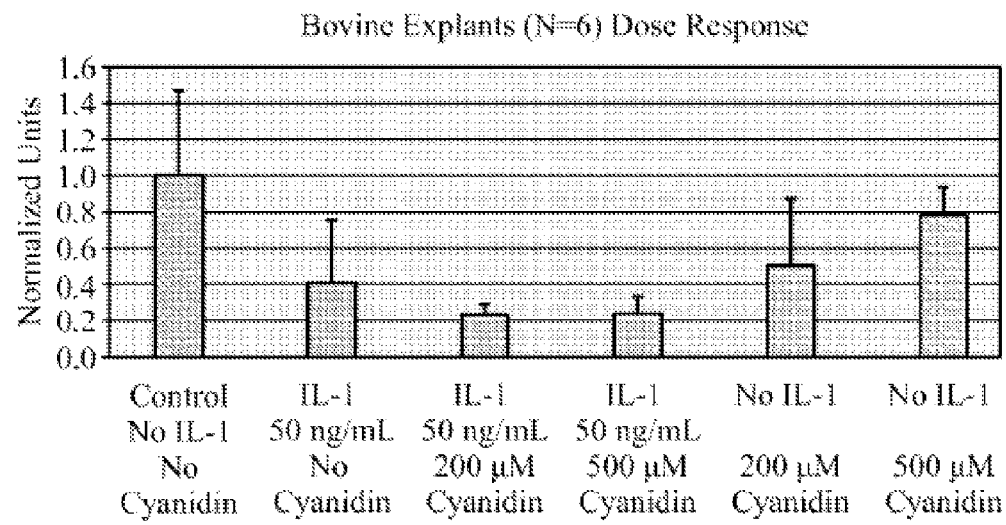
FIG. 9 depicts a chart demonstrating a dose response effect of cyanidin chloride on matrix synthesis in bovine cartilage explants (N=6) through the measurement of $^{35}S$ uptake.
Figure 10:
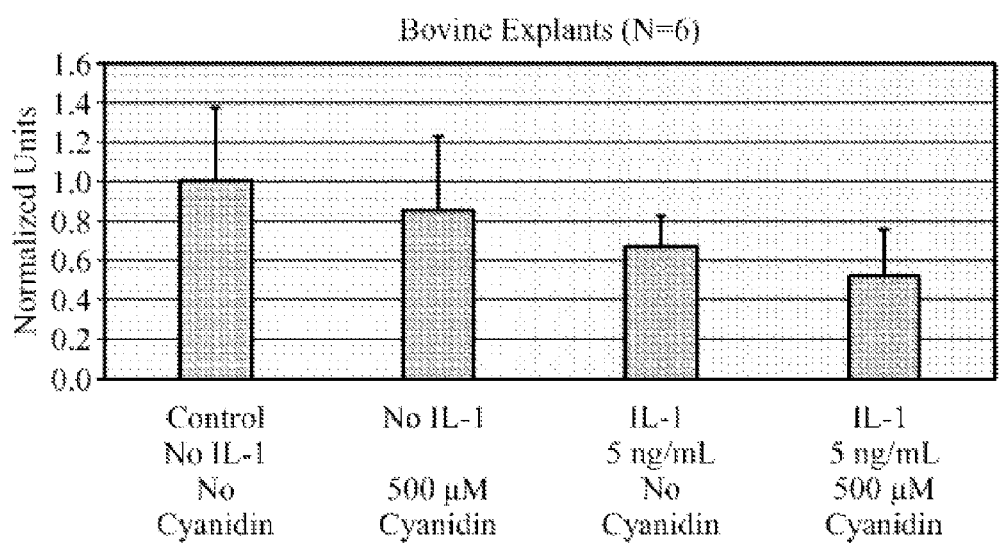
FIG. 10 depicts a chart demonstrating a repeated experiment to assess a potential dose response effect of cyanidin chloride on matrix synthesis in bovine cartilage explants (N=6) through the measurement of $^{35}S$ uptake.
Figure 11:
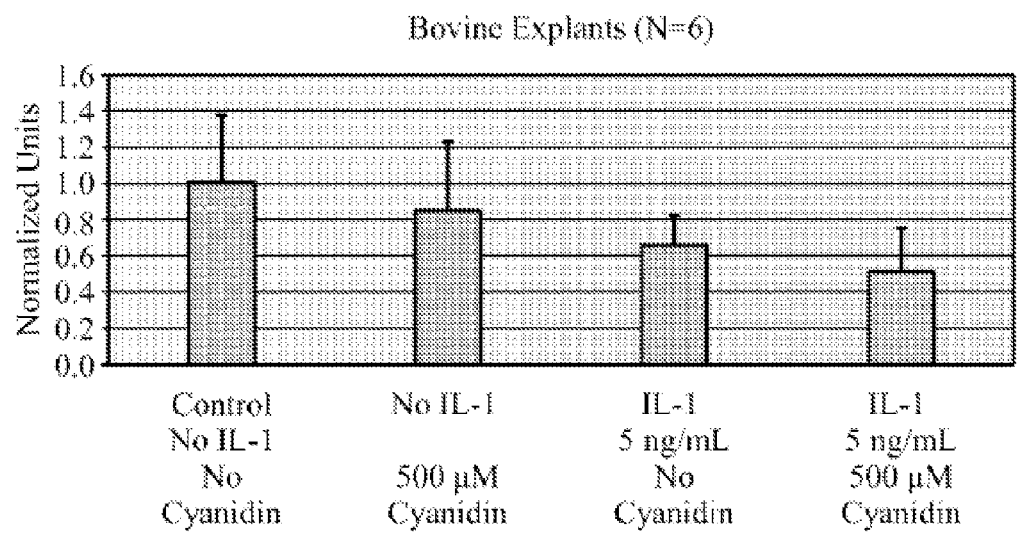
FIG. 11 depicts a chart demonstrating a repeated experiment to assess a potential dose response effect of cyanidin chloride on matrix synthesis in bovine cartilage explants (N=6) through the measurement of $^{35}S$ uptake.

Referring collectively to FIGS. 3-8, it was found that in human explants cyanidin successfully increased IGF-1 gene expression more than kuromanin compared to the catabolic IL-1 alone. It was also found that IGF-1 production was increased in both cyanidin and kuromanin compared to IL-1 alone; however, the results did not appear consistent. Further research reveals the difficulty in using human explants. For instance, even using identical harvest and culture conditions, human articular chondrocytes from different individuals display extreme variability in their in vitro chondrogenic capacity. Grogan et al., Arthritis & Rheumatism, 2007 Feb. 2; 56(2)586-95. In addition, age-associated changes have also been found when using human articular chondrocytes. Barbero et al., OsteoArthritis and Cartilage, 2004; 12:476-84. While probative as to the effect on chondrocytes, use of in vitro human chondrocytes is yet to be conclusive. As such, studies were also conducted using an accepted bovine model to confirm positive results. Referring to FIGS. 9-11, matrix synthesis was determined by measuring 35S uptake in the presence of catabolic IL-1 and cyanidin. Initially a dose response was identified but difficult to reproduce.

Though there was some variation between experiments, it was apparent that the anthocyanin increased IGF-1 gene expression and increased IGF-1 production. Thus, the anthocyanins/anthocyanidins are believed to operate at least in part, through IGF-1. IGF-1 values in synovial fluid have been shown to correlate with osteoarthritic changes within the joint, independent of age and IGF-1 is lower in synovial fluid than in serum. Lis et al., Chir Narzadow Ruchu Ortop Pol., 2005; 70(6):407-10. Since, IGF-1 is present in the synovial joint in small amounts and the results show anthocyanins increase IGF-1 gene expression and production, the administration of composition including anthocyanin will effectively modulate the activity or gene expression of IGF-1, which in turn modulates the expression of IGF-1 in the synovium. Increasing expression of IGF-1 may counteract the presence of IGFBPs and thus increase the localized concentration of available IGF-1 for interaction with chondrocytes to prevent the degradation of cartilage. Further, since the half-lives of anthocyanins are quite short, gene expression and thus interaction of IGF-1 with cartilage can be effectively controlled.

Since the present invention does not require the administration of exogenous IGF-1 or human growth hormone (HGH) to increase localized concentrations of IGF-1 in the joint, many of the traditional concerns regarding administering such compounds can be avoided. That is, by tightly controlling the modulation of the endogenous IGF-1 gene itself, the present invention is subject to homeostasis protection of the body for safety. Accordingly, this approach is less likely to cause a variety of cancers and deleterious effects implicated with exogenous administration of IGF-1 or HGH.

It was hypothesized that the glycoside of anthocyanin may in fact stimulate the synovium to produce IGF-1 since anthocyanins are glycosides of anthocyanidins. Accordingly, anthocyanidins and their corresponding sugar-free anthocyanins were studied to determine if the sugar moiety was important for chondroprotective activity. It was found that the sugar moiety was not required for chondroprotection and thus also suggests the region may be modified to affect the properties of the composition without adversely affecting its activity. Though not yet confirmed, the sugar may in fact contribute in part to chondroreparative activity after cleavage.

While anthocyanins were demonstrated to provide chondroprotective activity, experiments were also conducted to assess whether the activity could be enhanced when provided as a combination treatment. Specifically, studies were conducted to assess whether synthesis of cartilage could be performed when combining an anthocyanin with glucose. In culture, cyanidin-3-glucoside, delphinidin-3-glucoside, pelargonidin-3-galactoses and pelargonidin were found to stimulate insulin secretion from rodent pancreatic beta-cells when provided with 4 and 10 mM glucose. Nair et al., J Agric Food Chem, 2005 Jan. 12; 53(1):28-31. Insulin is known to bind to the IGF-1 receptor and to illicit significant responses in cartilage. Kellner et al., 0.1 Drug Target, 201; 9(6):439-8. Water-soluble polyphenol polymers from cinnamon were also found to increase insulin dependent glucose metabolism roughly 20 fold and may potentiate insulin action. Anderson et al., J Agric Food Chem, 2004; 52(1): 65-70. Accordingly, it may be that anthocyanins or anthocyanidins, which have a generally polyphenol structure function in part as insulin secretegogues.

Figure 12:
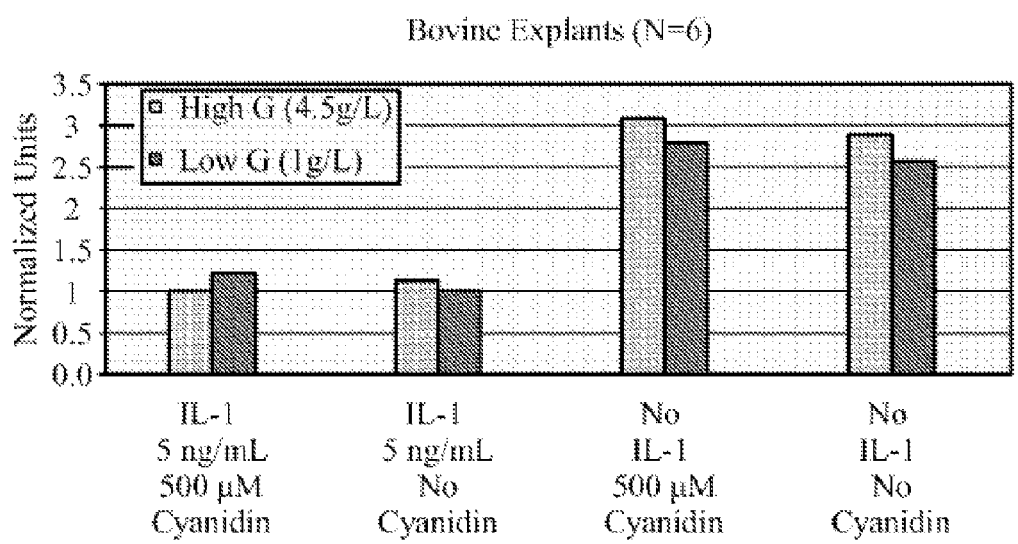
FIG. 12 depicts a chart summarizing matrix synthesis in bovine explants through measurement of $^{35}S$ uptake after exposure to 500 uM cyanidin chloride together with low glucose (1 g/L) or high glucose (4.5 g/L) in comparison to control.
Figure 14:
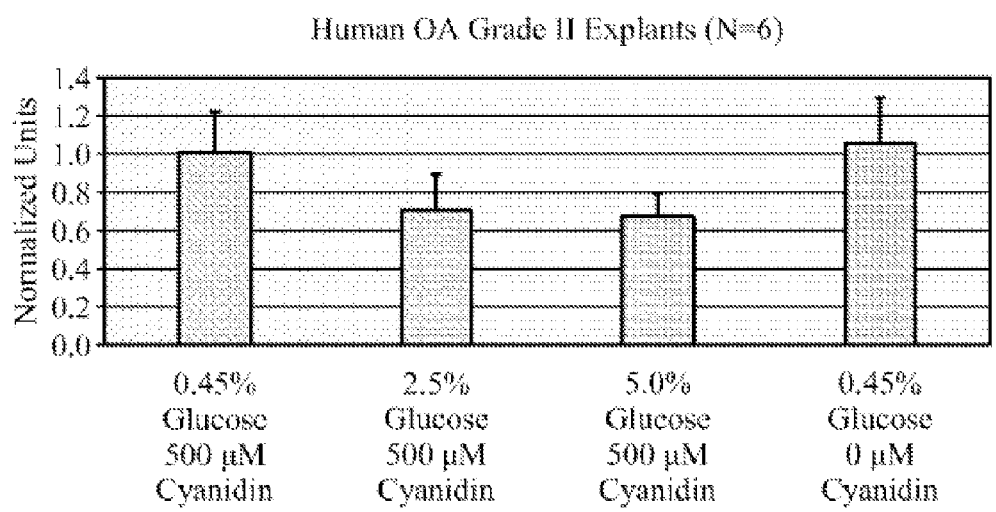
FIG. 14 depicts a chart summarizing the measurement of matrix synthesis in human osteoarthritic cartilage grade II-III explants using $^{35}S$ uptake analysis after treatment with 500 uM cyanidin chloride with physiologic (0.45%) or supraphysiologic (2.5% and 5%) concentrations of glucose.
Figure 15:
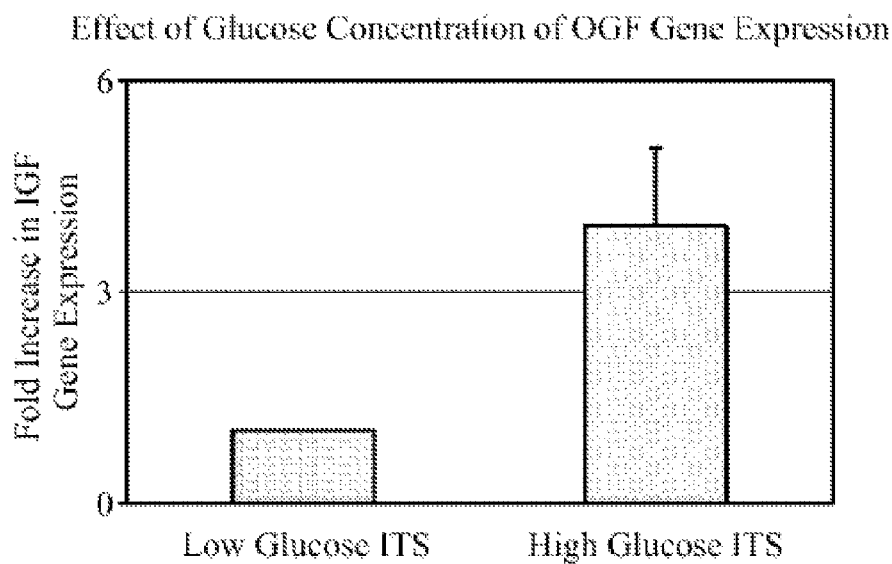
FIG. 15 depicts a chart of IGF-1 gene expression in human synovial explants after administration of low glucose (1 g/L) and high glucose (4.5 g/L).
Figure 16:
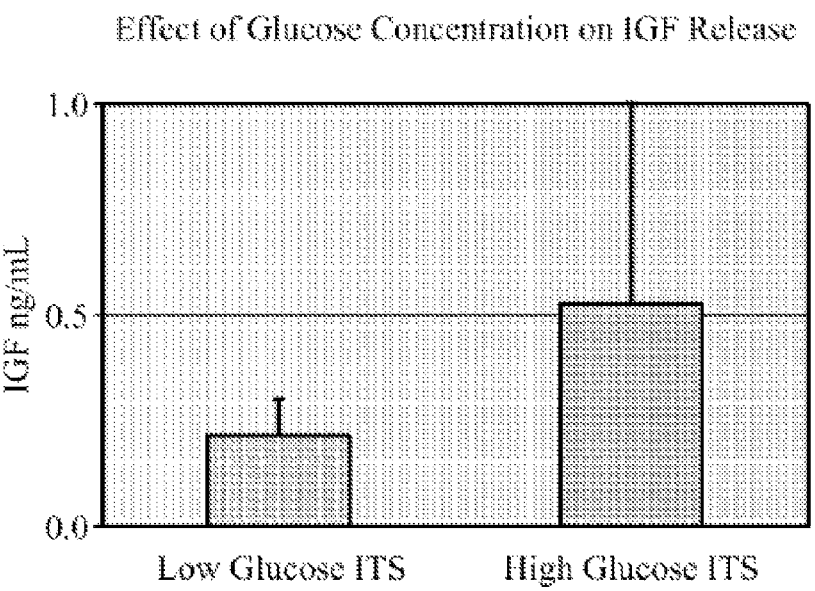
FIG. 16 depicts a chart of IGF-1 release from human synovial explants after administration of low glucose (1 g/L) and high glucose (4.5 g/L).

Referring to FIG. 12, matrix synthesis was assessed using the $^{35}$S uptake assay and in the presence of IL-1. When combined with glucose, significant update of $^{35}$S was measured, indicating that when combined, cyanidin and glucose significantly induce chondroreparative activity. Testing was further conducted to assess various concentrations of glucose together with cyanidin. Referring to FIGS. 14-16, low glucose appeared to stimulate matrix synthesis more than higher concentrations of glucose in human OA grade II explants: however, high glucose appeared to increase both IGF-1 gene expression and IGF-1 release. Thus, when combined with anthocyanin it appears the preferred concentration is about 0.5% glucose.

Further studies were conducted to assess the combination of higher and lower glucose concentrations together with anthocyanins/anthocyanidins in synovial explants. Referring to FIGS. 21-28, initially higher glucose levels together with cyanidin showed the highest levels of IGF-1 in media: however, when volumes were titrated to match the weight of the tissue, it appeared that lower glucose levels together with cyanidin and kuromanin had the greatest production of IGF-1 protein levels. Elevated IGF-1 gene expression was also found to significantly increase in synovial tissue after the addition of glucose. Though there appeared to be some variation between samples, the studies confirmed cyanidin and kuromanin together with glucose elevate IGF-1 gene expression and production.

While anthocyanins were shown effective at increasing IGF-1 gene expression and production, toxicity studies were required to assess the safety of administering the composition. As such, toxicity studies were conducted to assess the safety of exemplary anthocyanins: cyanidin, delphinidin and kuromanin Referring to FIGS. 17-18, 100 uM concentration appeared nontoxic, while 200 uM or greater may provide some toxicity. Accordingly, in preferred embodiments anthocyanins or anthocyanidins are proved in concentrations of about 100 uM or less.

Anthocyanins were also examined for potential anabolic effects and anti-arthritic effects. Referring to FIGS. 19-20, anthocyanins had no effect on matrix synthesis at 6 hours, delphinidin-3-O-glucoside had an anti-arthritic effect at 12 and 24 hours, and kuromanin chloride had a synergistic effect on matrix synthesis rates at 24 hours when combined with TGF-β.

Figure 29:
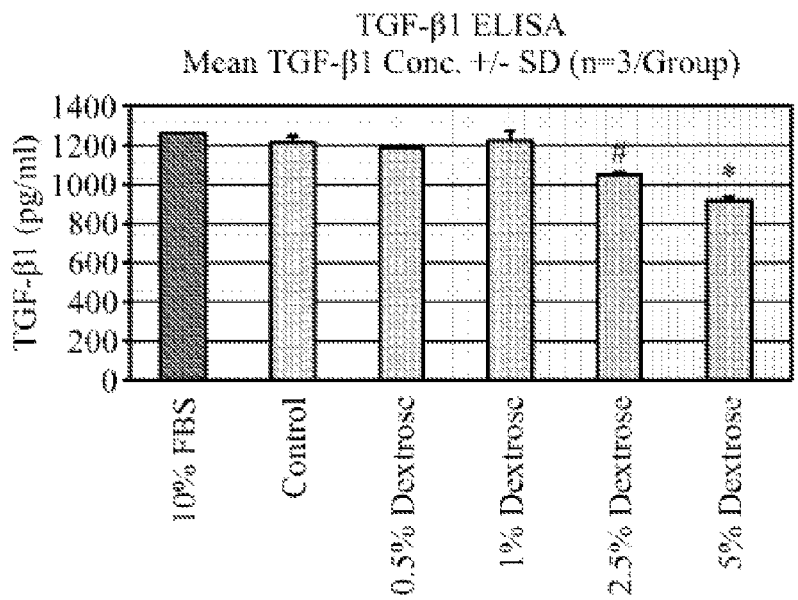
FIG. 29 depicts a graph demonstrating TGF-β concentration measured by ELISA after exposure of various concentrations of dextrose to fibroblast cells.
Figure 30:
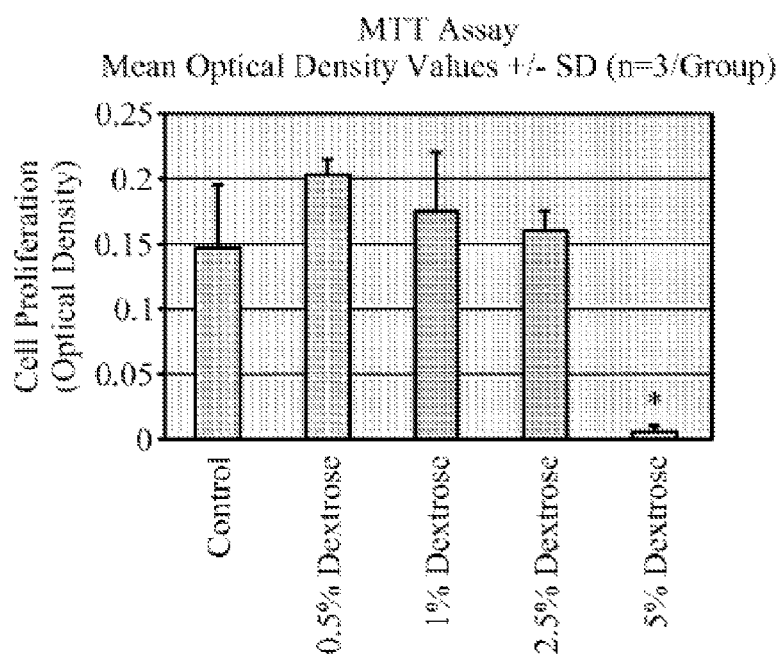
FIG. 30 depicts a graph demonstrating fibroblast cell proliferation after the administration of varying concentrations of dextrose.

For completeness, the relationship between a saccharide (dextrose) and TGF-β was also examined. Fibroblasts were treated with varying amounts of dextrose and measured for the release of TGF-β. Referring to FIG. 29, it appears dextrose does not increase TGF-β expression. In fact, higher amounts of glucose actually decreased the presence of TGF-β. However, referring to FIG. 30 when measuring cell proliferation, lower concentrations of glucose increased cell proliferation; whereas higher concentrations did not. It appeared that 0.5% glucose provided the greatest proliferation of fibroblasts.

Although various growth factors have been proposed to repair cartilage, their exogenous administration appears to coincide with deleterious effects. However, it is also shown that these growth factors, which do have beneficial activities in vivo can be modulated by the administration of compounds that are biologically safe. As such, the activation of beneficial endogenous growth factors may be tightly controlled using the compositions and methods herein.

Also, the intra-articular injection of growth factors, such as transforming growth factor-B1, insulin-like growth factor-1, and bone morphogenetic proteins, has been studied on the basis of abundant data from in vitro studies demonstrating the chondrogenic effects of these agents. Cuevas et al. reported preliminary data suggesting an early stimulating effect from basic fibroblast growth factor that had been injected with an osmotic pump into the knees of rabbits in which small (two-millimeter) defects had been created. Neidel found that intra-articular injections of insulin-like growth factor-1, fibroblast growth factor, or epidermal growth factor had no effect on the healing of standard cartilage defects. Although the data are still somewhat sparse, problems such as formation of osteophytes in association with intra-articular administration of transforming growth factor-131 might limit the usefulness of this technique. See O'Driscoll, Journal of Bone and Joint Surgery, 1998; 80:1795-1812.

The present invention demonstrates the effectiveness of a composition including an anthocyanin or anthocyanidin and glucose for the treatment of a cartilage-associated disorder. In particular, the composition may be chondroprotective or chondronutritive and thus protect against the degradation of cartilage and be chondroreparative or chondroregenerative and thus enhance cartilage production and restore normal activity of patterns.

The methods of repairing or regenerating cartilage as provided herein may include administering anthocyanin or anthocyanidin and glucose in a therapeutically effective amount or dose. The therapeutically effective dose of the composition will result in localized delivery of anthocyanin or anthocyanidin and glucose to the area of the affected joint. Preferably, the therapeutically effective dose is administered intra-articularly or juxta-articularly to the joint in need of treatment. This can be done by injection or infusion. The composition may be administered as a single dose or may be administered periodically over time. As such, administration may occur over many days or months. Further, administration of the composition may occur at regular or irregular time periods. Following a hiatus, subsequent administration may be instituted.

The therapeutically effective dose may vary depending on a variety of factors. For instance, the dose may vary depending on the form of the composition, such as a solution, a suspension, an emulsion, or a sustained release formulation. More specifically a sustained release formulation would tend to have a higher concentration of active components. Additional factors may include the subject's condition or progression of disease, whether additional therapies are being provided concurrently and the like. Further, consideration may include the presence or amount of effusion or inflammation of the joint. As general guidance the administered dose of anthocyanin or anthocyanidin may be in the range of about 0.002 mg to about 100 mg per joint. Preferably the anthocyanin is provided at about 100 uM or less. As general guidance, cyanidin chloride has a MW of about 322.7 and thus 100 uM is equivalent to about 0.32 mg/10 mL; kuromanin chloride has a MW of about 484.84 and thus 100 uM is equivalent to about 0.485 mg/10 mL; and delphinidin-3-glucoside has a MW of about 500.8 an and thus 100 uM is equivalent to about 0.501 mg/10 mL. Glucose or dextrose may be provided in concentrations from about 0.5 mM to about 100 mM. However, the present invention is non-limiting with respect to concentration as long as a beneficial effect results. In some embodiments a 5% or 10% glucose solution includes anthocyanin or anthocyanidin. In some embodiments glucose is provided at about 0.5%. Amounts greater or lesser than the ranges provided are also encompassed by the instant invention. One skilled in the art will realize that the dose by injection will likely be less than that of an oral medication since the oral medication must clear numerous barriers. Further, since according to Frei, the vast amount of flavonoids are cleared quickly through the urine and bile, an oral composition would need to account for its rate of excretion. Thus, it may be that the anthocyanins are broken down to phenolic acids and aldehyde as suggested by Woodward et al.

While it is presumed that the anthocyanin/anthocyanidin provides chondroprotective activity in vivo upon injection, it may be that a metabolite of the anthocyanin or anthocyanidin is providing chondroprotective or chondroreparative activities. Again, anthocyanin metabolites have been identified in urine and serum. Kay et al. Br J Nut; 2004 June; 91(6):933-42. Thus, downstream metabolites of anthocyanin and anthocyanidin, such as phenolic compounds are also encompassed by the methods of the present invention.

Though non-limiting it is believed that the composition stimulates production of cartilage indirectly. That is, the composition is administered to the synovium, such as by injection, where it increases IGF-1 gene expression and production of IGF-1 itself Increased amounts of IGF-1 are released into the joint where soluble IGFBPs are present. Though the IGF-1 population is partially bound, increasing the localized concentration of IGF-1 increases the available IGF-1 for binding to receptors at the cartilage, which induces cartilage formation.

It may be that the composition stimulates production of the cartilage directly. That is, while the traditional view of articular cartilage is that it is non-regeneratative, emerging research shows that the articular cartilage may in fact have distinct zones with different cellular and molecular phenotypes and the superficial zone may in fact harbor stem cells. Karlsson et al., Arthritis Research and Therapy 2009; 11:121. Mesenchymal stem cells (MSCs) have been isolated from the synovial membrane and synovial fluid and are believed to have immunosuppressive and anti-inflammatory effects. Chen et al., Arthritis Research and Therapy 2008: 223. For instance MSCs can be isolated from the synovial membrane of knee joints and when cultured maintain their multilineage differentiation potential. De Bari et al., Arthritis and Rheumatism, 2001 August; 44(8):1928-1942. Accordingly, it may be that the composition of the present invention acts on cartilage, such as through stem cells found in the superficial zones in addition to the synovial membrane.

The compositions provided herein may act in part as an anti-inflammatory. Antioxidants have been proposed to have anti-inflammatory activity and anthocyanins are known to have antioxidant properties. In addition, antioxidants have been proposed as potentially reversing cartilage tissue damage caused by cytokines. Homandberg et al., Biochimica et Bioyphysica Acta 1996; 1317(2):143-8.

While the composition is effective alone, it may also be used in a combined therapy. For instance, the composition may be combined with surgical methods, coadministered with a synovial explant or explant of synovial villi, or may be combined with therapies directed towards reducing load on an affected joint.

In some embodiments, the compositions of the present invention are administered in combination with a surgical method. For example, the compositions according to the present invention may be given at the time of surgery or after surgery. The compositions may be provided as a combined therapeutic or may assist in healing or recovery after surgery. Nonlimiting examples of surgical procedures that may be combined with the compositions of the instant invention include arthroscopy, arthroscopic surgery, anthroplasty, osteotomy, cartilage, meniscal or ligament repairs, reconstruction, resection and the like. In some embodiments treatment with the composition is preceded by joint lavage and/or vacuum to remove debris and/or to dilute cytokines or fibronectin. In some embodiments, the compositions treat or prevent post-traumatic osteoarthritis, which may follow joint surgery.

In some embodiments of the present invention, the synovium tissue is harvested, treated with the composition according to the present invention, and administered to the subject in need of treatment. The synovium tissue may be treated in toto (or with all of its components) or cells may be extracted or isolated from the synovium then treated and later implanted. In further embodiments, the composition is provided together with synovial villi as an explant. In some instances the synovial villi are cultured in the presence of the composition. In other embodiments, the synovial villi are provided as explants and introduced to the site of injury followed by or concurrently with administration of the composition. The synovial villi may be particularly desirable in combination with the composition since they may be rich in stem cells and IGF-1, which may be modulated by the composition to affect differentiation or to further increase IGF-1. U.S. patent application Ser. No. 11/210,077 describes the use of synovium explants including synovial villi and is herein incorporated by reference.

In some embodiments of the present invention, the composition is administered in combination with a decrease in weight bearing of joints, such as during a recovery phase, such as after a surgical procedure. Thus, in some embodiments the composition is provided together with a device or procedure which selectively unloads an affected joint. Such devices include unloader knee braces and medial and/or lateral wedged insoles. U.S. patent application Ser. No. 12/603,160 describes the use of wedged insoles and is herein incorporated by reference.

Compositions

The preferred compositions include anthocyanins or anthocyanidins and glucose. Preferably, the compositions are provided with a pharmaceutically acceptable carrier. Preferably, the composition is provided as a solution for injection or infusion or one that can be suspended such that it can be injected or infused at the site requiring treatment such as in proximity to or intra-articularly to a joint requiring the provided methods.

Over 300 structurally distinct anthocyanins have been identified in nature. Among these include a variety that are currently being evaluated for their ability or desirability to prevent the degradation of cartilage or repair or regenerate cartilage, including kuromanin (cyanidin-3-glucosidase), delphinidin-3-glucosidase, cyanidin-3-galactosidase and pelargonidin-3-galactosidase. Anthocyanins for use with the present invention include those that are isolated or purified from nature or chemically synthesized. Specifically, anthocyanins and anthocyanidins tested are that are commercially available and provided consistent with pharmacologic standards. Such compounds are well characterized and adapted for pharmaceutical administration. Further, anthocyanins may be chemically modified to form a derivative or structural analog, which may affect one or more characteristics, such as to increase or decrease solubility, activity, stability, bioavailability and the like. Such modifications may include the addition of one or more substituents or side chains including an alkyl or alkoxy group, a hydroxyl group, an ester and the like. Though non-limiting, derivatives and analogs may be formed using standard organic chemistry techniques such as through the use of enolate intermediates, electrophilic or nucleophilic attack, and the like. The derivative should not destroy the activity of the composition and should not confer toxic properties.

Anthocyanidins are the sugar free counterparts of anthocyanins. They are salt derivatives of the 2-phenylchromenylium cation, also known as flavylium cation. When used in the present invention, the cation may be provided with a suitable counter ion, such as but not limited to chloride. Non-limiting examples of anthocyanidins encompassed by the present invention include aurantinidin, cyanidin, delphinidin, europinidin, luteolinidin, pelargonidin, malvinidin, peonidin, petunidin and rosinidin. The anthocyanidins may be isolated or purified from nature or may be chemically synthesized. In addition, derivatives or analogs may be formed to affect solubility, activity, stability, bioavailability and the like. Exemplary anthocyanin and anthocyanidin structures are provided in Table 1, which provides "R" groups depicting regions of likely substitutions to generate various analogs.

TABLE 1

Anthocyanidin core structure

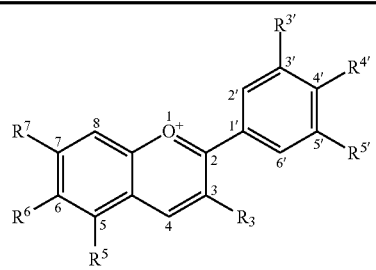

Kuromanin chloride

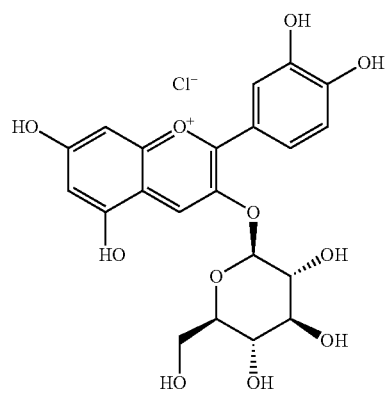 [SMILES: OC[C@H]1O[C@@H](Oc2cc3c(O)cc(O)cc3[o+]c2-c2ccc(O)c(O)c2)[C@H](O)[C@@H](O)[C@@H]1O ; [Cl-]]

Cyanidin

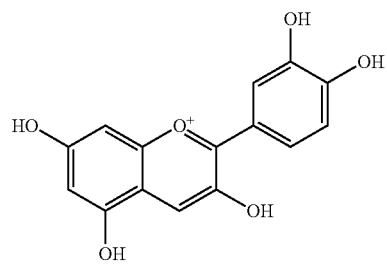 [SMILES: Oc1cc(O)c2cc(O)c(-c3ccc(O)c(O)c3)[o+]c2c1]

Delphinidin

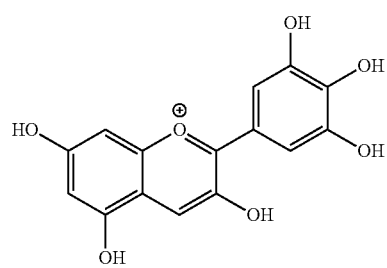 [SMILES: Oc1cc(O)c2cc(O)c(-c3cc(O)c(O)c(O)c3)[o+]c2c1]

TABLE 1-continued

Perlargonidin

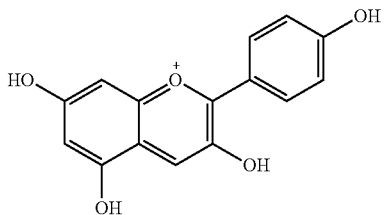

It has been hypothesized that the glycoside of anthocyanin may stimulate the synovium to produce insulin-like hormone since anthocyanins are glycosides of anthocyanidins. Accordingly, anthocyanidins and their corresponding sugar-free anthocyanins were studied to determine if the sugar moiety was important chondroprotective activity. It was found that the sugar moiety was not required for chondroprotection and thus also suggests the region may be modified to affect the properties of the composition without adversely affecting its activity. Though not yet confirmed, the sugar may in fact contribute in part to chondroreparative activity after cleavage. In this case, the reagent would act as both catalyst in the general sense and substrate in the process of the cartilage repair. That is, the cleaved saccharide itself may be used as a substrate in the formation of new cartilage.

In preferred embodiments of the present invention, the anthocyanin or anthocyanidin is provided in combination with a sugar, most preferably glucose. Glucose is a monosaccharide and is an important carbohydrate in biology. Two stereoisomers of the aldohexose sugars are known as glucose, L-glucose and D-glucose. D-glucose is also commonly referred to as dextrose. Park et al. previously demonstrated that injection of 10% dextrose protects cartilage in the knee from breakdown after cutting the ACL ligament in rabbits. Animal Research & Therapy, 2007; 9(1):R8. In addition, Reeves et al. demonstrated a benefit in humans when injecting severely arthritic knees with 10% dextrose. Alth Ther Filth Med 2002; 6(2):37-46. Reeves also showed a benefit when injecting an arthritic thumb with dextrose. J Altern Complement Med. 200; August; 6(4):311-20. As provided herein, these benefits can be enhanced by co-administration of glucose or dextrose with anthocyanin or anthocyanidin.

Low and high glucose conditions were provided in culture to assess the anthocyanin/anthocyanidin alone and in combination with glucose. Physiologic concentration of glucose was provided as 0.45%, which mimicked the natural glucose levels in the articular joint. Under low glucose levels (2.5%), cyanidin showed some chondroprotective activity. However, chondroprotective activity was nearly 20% greater in higher glucose conditions (5%).

Glucose itself may also function as a carrier or vehicle for administering the anthocyanin/anthocyanidin, thereby forming two functions. A variety of glucose-related carriers are known in the pharmaceutical arts and incorporated herein.

For purposes of the present invention, the pharmaceutical composition including an anthocyanin or anthocyanidin is preferably formulated in a unit dosage and in an injectable or infusible form such as solution, suspension or emulsion. It can also be in the form of a lyophilized powder, which can be converted into solution, suspension or emulsion before administration. In some embodiments a pharmaceutical composition is provided in a formulation that includes biodegradable microspheres or of amorphous bioadsorbable material of glucose itself. The common biodegradable carriers are importantly amorphous physically and as opposed to crystalline material, do not cause tissue irritation. In some preferred embodiments the composition is administered together with 50/50 D, L. lactide/glycolide or 85/15 D,L lactide glycolide. Also encompassed herein are nanospheres as known in the pharmaceutical arts. The pharmaceutical compositions may be sterilized by membrane filtration, autoclaving, irradiation and the like and may be stored in unit-dose or multi-dose containers such as sealed vials or ampules. As a non-limiting example, a dose pack may contain 3-5 vials for administration. The first injected initially at the office or at surgery then the remaining vials to be administered over time, such as periodically over weeks. In some instances, glucose may form a portion of the delivery vehicle, whereupon release it enhances the chondroreparative features of the composition.

Toxicity studies on human articular chondrocytes in culture were performed with cyanidin chloride, kuromanin chloride, delphinidin-3-0-glycolide, and pelargonidin chloride. Each were non-toxic at concentrations up to 100 uM. Cyanidin chloride, kuromanin chloride, and delphinidin-3-O-glucoside induced cell death at concentrations at or above 200 uM. Thus, concentrations of about 100 uM or less are particularly preferred.

Methods of formulating pharmaceutical compositions are generally known in the art and are applicable with the instant invention. For instance, the active ingredients may be mixed together with the pharmaceutically acceptable carrier or salt. Thorough discussions of formulation development and selection of pharmaceutically acceptable carriers, stabilizers, coloring and flavoring agents and like can be found in a variety of pharmaceutical texts known to those skilled in the art, such as *Remington's Pharmaceutical Sciences* (Mack Publishing Co., Eaton, Pa.), the contents of which are herein incorporated by reference in its entirety.

Again, in some embodiments, the compositions of the present invention are formulated in a sustained-release formula to prolong the presence of the compounds in the treated subject, generally for longer than one day. Many methods of preparing sustained release formulations are known in the art and are available in a variety of publications, including *Remington's Pharmaceutical Sciences*, cited and incorporated by reference above. In some instances, the anthocyanin or anthocyanidin and optionally glucose is trapped in semi-permeable matrices of solid hydrophobic polymers. The matrices can be shaped into films, coatings, microcapsules or microspheres and administered as known by those skilled in the appropriate art. Any suitable ratio may be used, which may in part depend on the desired matrix. As a nonlimiting example, the pharmaceutical may be provided with a biodegradable polymer formed from about 85/15 or 50/50 D, L lactide/glycolide. The matrices may be a variety from a variety of materials; solids and meshes.

While the invention has been described in connection with specific embodiments thereof, it will be understood that it is capable of further modifications. Accordingly, it will be appreciated by those skilled the art that the same can be performed within a wide variety of parameters, concentrations and conditions without departing from the spirit and scope of the invention and without undue experimentation.

EXAMPLES

Example 1: Chondroprotective Effect of Kuromanin and Cyanidin in Human Chondrocytes and Cartilage Explants The chondroprotective effect of kuromanin and cyanidin is shown in human cartilage explants and in cultured chondrocytes. In summary, both kuromanin and cyanidin are effective chondroprotective agents limiting the degradation of human cartilage against the catabolic effects of IL-1. In addition, kuromanin and cyanidin may promote anabolism through enhanced production of IGF-1 or by reducing suppression of IGF-1.

Materials and Methods

Human osteoarthritic cartilage samples were procured through the Tissue Procurement Facility of the University Hospitals of Cleveland/Case Western Reserve University and with prior approval of the IRB of University Hospitals of Cleveland. The cartilage samples were obtained from patients undergoing total anthroplasty of the knee due to degenerative joint diseases. In all cases care was taken to use only "macroscopically normal" cartilage samples. No samples were exposed to radiation solely for the purpose of these studies but almost all patients will have received X-rays as part of their clinical presentation during the execution of care. The same donor tissue was not used in all experiments but untreated controls were included in all protocols.

Cartilage Explants.

Full thickness cartilage slices (20-25 mg) were dissected from the cartilage using a sterile scalpel blade. Four to five cartilage pieces that were approximately equal in size and weight were transferred to each well of a 24-well, flat bottom plate (Nuns, Denmark) containing DMEM:F12 (1:1) supplemented with antibiotics and 10% FCS and cultured for 24 hours. Subsequently the cartilage explants were cultured overnight in serum free media. The cartilage explants were treated with IL-$\beta$ alone or with IL-$\beta$ positive test agents for 72 hours in serum free media. Explants cultured in the absence of IL-$\beta$ or test agents were used as controls. Additionally, the actions of kuromanin or cyanidin chloride were examined independently of IL-$\beta$ exposure (5 ng/mL). Where appropriate, explants were exposed to test agents 15 minutes prior to the treatment with IL-$\beta$. Total glycosaminoglycan present in the culture supernatant was estimated as described below.

Primary Cultures of Human Chondrocytes.

Chondrocytes were prepared by the enzymatic digestion of knee cartilage, as previously described. (Ahmed S et al., J Nutr 2005 135:20962102). Chondrocytes were plated ($1 \times 10^6$ cells/mL) in 35 mm culture dishes (BD, Mountain View, Calif.) and cultured in DMEM:F12 (Mediatech, Herndon, Va.) supplemented with 10% FCS and 1% Penn:Strep for 72 hrs at 37° C. and 5% CO2 in a tissue culture incubator. Chondrocytes were serum starved overnight and then exposed to either kuromanin or cyanidin chloride (5 or 50 ug/mL), prograde (2 or 10 ug/mL) alone or in combination in fresh serum-free medium for 1 hr prior to the addition of IL-$\beta$.

Real Time RT-PCR for IGF-1.

Total cytoplasmic RNA was prepared from primary cultures of human chondrocytes using a commercially available kit according to the instructions of the manufacturer (Qiagen, Valencia, Calif.). Real time quantitative RT-PCR with internal fluorescent hybridization probes was performed as previously described (Ahmed S et al., ECAM 2005 2:301-8) and the IGF-1 gene expression was quantified using a commercially available Gene Expression Assay kit (Applied Biosystems, CA). Expression of IGF-1 mRNA was normalized to 13-actin mRNA expression. and the results were expressed as fold induction relative to controls.

IGF-1 Production as Determined by ELISA.

Human IGF-1 label in chondrocytes culture or cartilage explant media was quantified using a commercially available Human IGF-1 ELISA kit (R& D Systems) per manufacturer's directions.

Cartilage Breakdown as Determined by GAG Release.

At the end of culture period, the culture medium was collected from each group. A 50 uL aliquot of collected supernatant from each sample was utilized to estimate the total glycosaminoglycan (GAG) concentration by a colorimetric method employing a DMMB as previously described (Miller M J S et al., BMC Complementary and Alternative Med 2006 6; 13). Color intensity was read spectrophotometrically at 535 nm using the Lambda 25 spectrophotometer (Perkin-Elmer, CT) and the values were derived from a standard curve prepared using different concentrations of chondroitin sulfate. Results are expressed as micrograms of glycosaminoglycan released per mg of cartilage tissue.

Results

Chondroprotection:

Suppression of IL-1 induced GAG Release. IL-1 induced gene expression and production of MMPS that acts to breakdown the cartilage matrix. This effect can be quantified in cartilage explants by the release of GAG (glycosaminoglycans) into the culture media.

Both kuromanin and cyanidin chloride were chondroprotective in this system at the doses used. There was no apparent difference in potency or efficacy between kuromanin and cyanidin chloride (see FIGS. 1 and 2). There is a suggestion that the highest dose of kuromanin tested possessed some catabolic effects that may reflect cell toxicity.

Referring to FIGS. 1 and 2, IL-1 promoted cartilage catabolism and this effect was blocked with both kuromanin and cyanidin chloride. There was a tendency for the high dose of kuromanin to promote GAG release under basal conditions, an effect not evident with cyanidin chloride where chondroprotection was evident. Kuromanin was abbreviated as KuCl (FIG. 1) and the non-glycosylated control cyanidin chloride was abbreviated as CC1 (FIG. 2).

Expression of IGF-1 in Human Chondrocytes.

Figure 3:
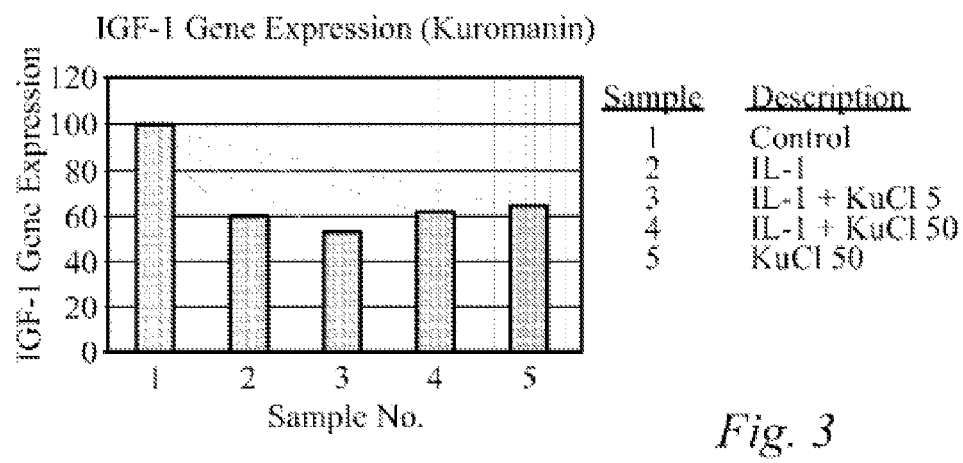
FIG. 3 depicts a chart summarizing IGF-1 gene expression data measured from human explant cultures as described in Example 1 for kuromanin. Sample 1 provides the control. Sample 2 was treated with IL-1 alone. Sample 3 was treated with IL-1 and KuCl at 5 ug/mL. Sample 4 was treated with IL-1 and KuCl at 50 ug/mL. Sample 5 was treated with KuCl at 50 ug/mL. In summary, IGF-1 gene expression was greater compared to IL-1 alone when treated with kuromanin at high dose.
Figure 4:
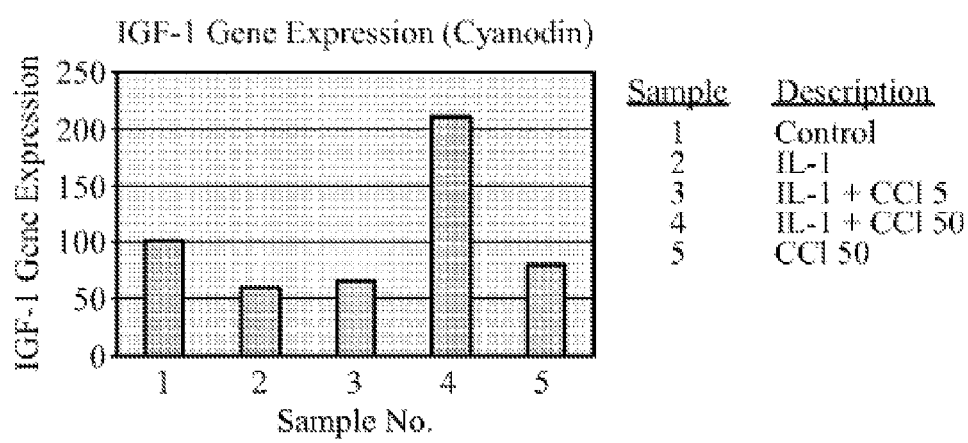
FIG. 4 depicts a chart summarizing IGF-1 gene expression data measured from human explant cultures as described in Example 1 for cyanidin. Sample 1 provides the control. Sample 2 was treated with IL-1 alone, Sample 3 was treated with IL-1 and CC1 at 5 ug/mL. Sample 4 was treated with IL-1 and CC1 at 50 ug/mL. Sample 5 was treated with CC1 at 50 ug/mL. In summary, gene expression was greater compared to IL-1 alone when treated with cyanidin alone or in combination with IL-1.

Referring to FIGS. 3 and 4, IL-1 suppressed IGF-1 gene expression by approximately 40%. When IL-1 was administered with kuromanin at 5 or 50 ug/mL there was no further changing in this pattern, with IGF-1 gene expression in chondrocytes remaining depressed. A similar pattern was noted with cyanidin with the exception that the 50 ug/mL does was elevated above control. Performed in duplicate this response seems to be anomalous. Indeed it is consistent with the inherent suppressive effects of 50 ug/mL of cyanidin.

IGF-1 Protein Production from Cultured Chondrocytes.

Media levels of IGF-1 were measured by ELISA. Exposure to IL-1 resulted in a reduction of IGF-1 production. When 1L-1 was administered with kuromanin there was a restoration of IGF-1 production. When IL-1 was administered with kuromanin there was a restoration of IGF-1 production at the low dose (5 ug/mL) but no effect over IL-1 with the high dose of 50 ug/mL. Additionally, the high dose alone of kuromanin reduced IGF-1 protein levels in the media to a similar level as to that seen with IL-1. With cyanidin there was no restoration of media IFG-1 levels with either dose and the high dose of cyanidin reduced IGF-1 production from control values. In general the effects of cyanidin and kuromanin on chondrocytes production of IGF-1 were consistent with their effects on IGF-1 mRNA levels (transcription). However, to evaluate the response, further the study was repeated in cartilaginous explants.

IGF-1 Production from Cultured Human Chondrocytes.

Figure 5:
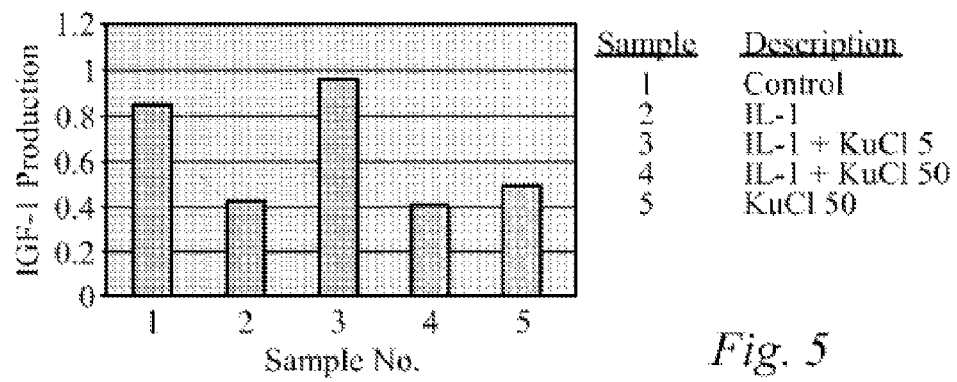
FIG. 5 depicts a chart summarizing IGF-1 production data measured from human chondrocytes in culture as described in Example 1 for kuromanin. Sample 1 provides the control. Sample 2 was treated with IL-1 alone. Sample 3 was treated with IL-1 and KuCl at 5 ug/mL. Sample 4 was treated with IL-1 and KuCl at 50 ug/mL. Sample 5 was treated with KuCl at 50 ug/mL. In summary, IGF-1 production was greater than IL-1 alone when treated with kuromanin at high levels and at low levels in combination with 1L-1.
Figure 6:
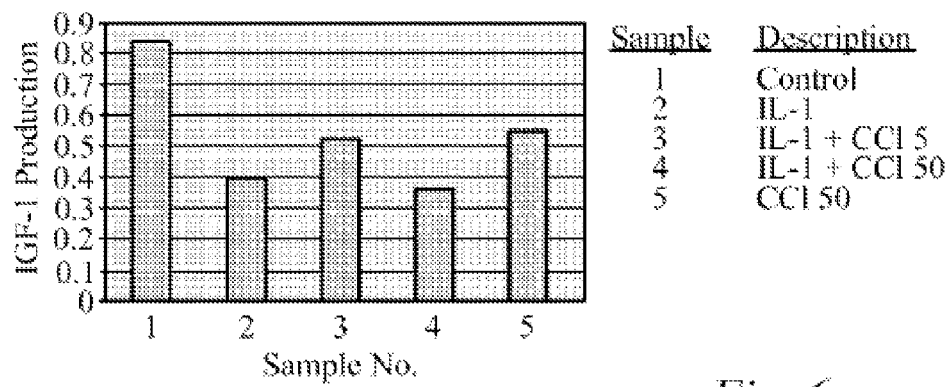
FIG. 6 depicts a chart summarizing IGF-1 production data measured from human chondrocytes in culture as described in Example 1 for cyanidin. Sample 1 provides the control. Sample 2 was treated with IL-1 alone. Sample 3 was treated with IL-1 and CC1 at 5 ug/mL. Sample 4 was treated with IL-1 and CC1 at 50 ug/mL. Sample 5 was treated with CC1 at 50 ug/mL. In summary, IGF-1 production was greater than IL-1 alone when treated with cyanidin alone at high levels and at low levels in combination with IL-1.
Figure 7:
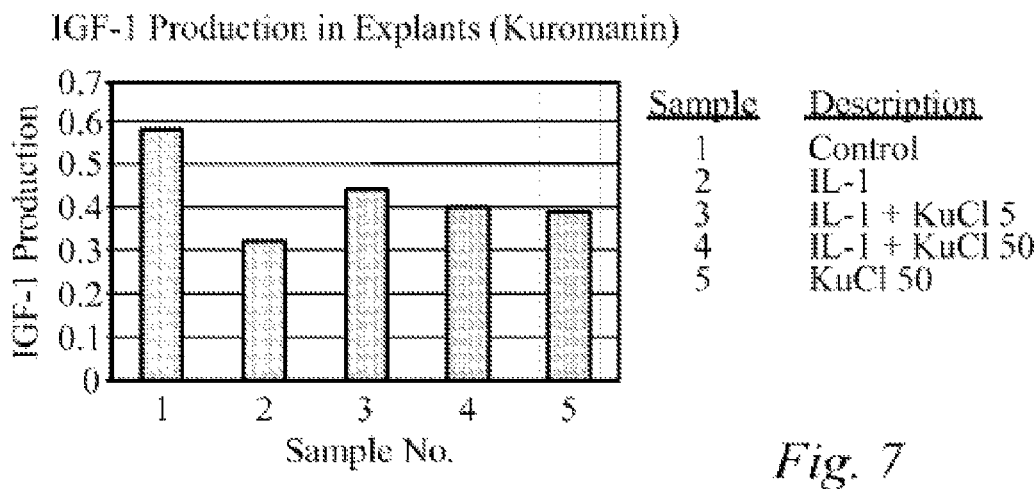
FIG. 7 depicts a chart summarizing IGF-1 production data measured from human cartilage explants as described in Example 1 for kuromanin. Sample 1 provides the control. Sample 2 was treated with IL-1 alone. Sample 3 was treated with IL-1 and KuCl at 5 ug/mL. Sample 4 was treated with IL-1 and KuCl at 50 ug/mL. Sample 5 was treated with KuCl at 50 ug/mL. In summary, IGF-1 production was greater than IL-1 alone when treated with kuromanin alone or in combination with IL-1.

IGF-1 production was determined in the explant media by ELISA. Chondrocytes were treated with IL-1 in the presence and absence of kuromanin or cyanidin (FIGS. 5 and 6 respectively). Reduced production of IGF-1 was found in cultured chondrocytes treated with either kuromanin or cyanidin.

IGF-1 Production in Explants of Human Cartilage.

Figure 8:
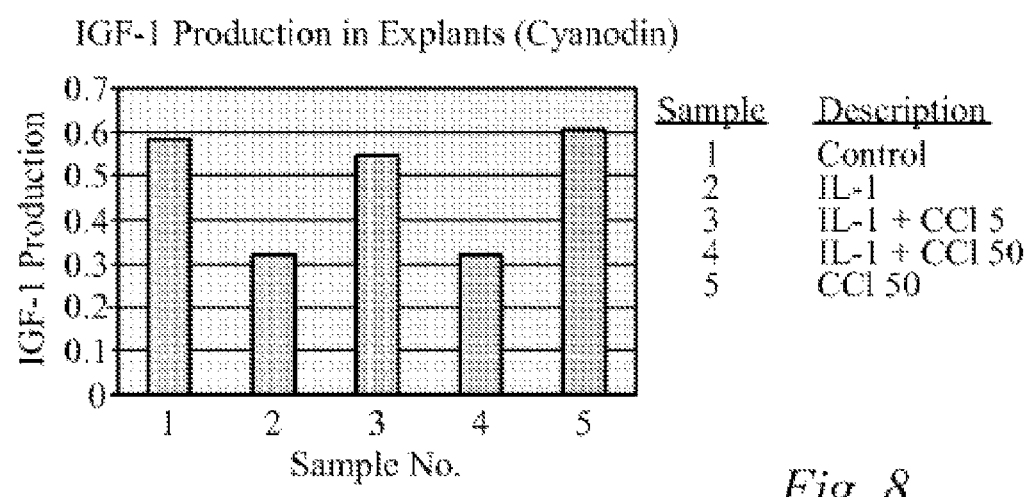
FIG. 8 depicts a chart summarizing IGF-1 production data measured from human cartilage explants as described in Example 1 for cyanidin. Sample 1 provides the control. Sample 2 was treated with IL-1 alone. Sample 3 was treated with IL-1 and CC1 at 5 ug/mL. Sample 4 was treated with IL-1 and CC1 at 50 ug/mL. Sample 5 was treated with CC1 at 50 ug/mL. In summary, IGF-1 production was greater than IL-1 alone when treated with cyanidin alone or in combination with IL-1.

IGF-1 levels in media from human cartilage explants were treated with IL-1 and/or kuromanin (FIG. 7) or cyanidin (FIG. 8). In explants treated with cyanidin, there was restoration of control IGF-1 production despite the presence of IL-1 with low dose cyanidin (5 ug/mL) but no benefit was observed with high dose cyanidin (50 ug/ml.). In contrast to kuromanin; however, high dose cyanidin did not express basal IGF-1 production in explants (FIG. 8), although both reduced production in cultured chondrocytes (see FIGS. 5 and 6).

Example 2: Kuromanin Protects and Promotes Cartilage Metabolism in Bovine Cartilage Explants in the Presence of IL-1.

After exposure of control bovine cartilage explants to kuromanin chloride increased production of mucopolysaccharides was observed. When preincubating bovine cartilage with IL-1 to form damaged tissue, the addition of kuromanin increased production of mucopolysaccharides.

Materials and Methods

Bovine cartilage explants were placed in culture including 10% FCS and Vitamin C. IL-1 was added to a test population and IL-1 was not added to control. Explants were cultured for 24 hours. Kuromanin chloride was then added to each culture. Mucopolysaccharides were measured using radioactive 35 Sulfur uptake.

Results

In each instance, kuromanin treatment resulted in an increase of mucopolysaccharide.

Example 3: Effect of Anthocyanin Treatment on Osteoarthritic Cartilage

The effect of cyanidin chloride with and without glucose was tested for its effect on reducing changes seen in osteoarthritis.

Cyanidin alone had an inconsistent effect on bovine cartilage explants at a dose of 500 uM but no effect on human OA explants. Increasing glucose concentration to 0.45% had a beneficial effect, but higher glucose dose (2.5% and 5%) reduced matrix synthesis. Combining cyanidin and glucose did not have significant synergistic effect.

Materials and Methods

Tissue Source and Harvest.

Bovine cartilage explants (full thickness, 6 mm in diameter) were harvested from fresh femoral condyles. Human osteochondral plugs were harvested using 6 mm osteochondral grafting donor tool (Arthrez 1981-06S, Naples, Fla.) from femoral condyles retrieved from total knee arthroplasty surgery that had been stored in DMEM at 20 degrees C. for less than 24 hours. Full-thickness cartilage explants were cut from the subchondral bone. Each of the 6 mm cartilage disks were divided into 4 equal quadrants. Each quadrant was placed in a different experimental group. This allowed for a paired comparison and controlled for differences in grade of arthritis, thickness of cartilage, cell density, etc. The explants were washed 4-5 times with DMEM with 10% calf serum and were allowed to stabilize for 24 hours in a tissue culture incubator. Explants were then serum starved (0.1% calf serum) for 24 hours prior to commencement of cyanidin chloride treatment.

Anthocyanin Treatment.

3 mL fresh media with 20 uCi/mL of $^{35}$S-labeled sodium sulfate (NEX0414 Perkin Elmer, Boston, Mass.) (DMEM with 10% CS) was added to each of the explants along with 30 uL of 50 mM stock cyanidin chloride (MW 322.7 g/mole) solution (diluted in DMSO) (Chromadex Inc., Irvine, Calif.) to give the final cyanidin chloride concentration of (200 or 500 uM) in culture. Explants were subjected to cyanidin chloride treatment for 48 hours.

Radioisotope Uptake Measurement.

Radioactive media was aspirated after 48 hours and explants were washed in ice-cold 1×PBS for 10 minutes×3. Each cartilage explant quadrant was blotted dry and was placed in 500 uL of 2 mg/mL Proteinase K (Fisher Scientific, Fair Lawn, N.J.) in TE Buffer solution (10 mM Tris, 1 mM EDTA) and was allowed to rotate at 57 degrees C. for 24 hours in a hybridization oven until completely dissolved. Quantification of $^{35}$S-labeled proteoglycans complexed to alcian blue by rapid filtration in multiwall plates was adopted and modified from Masuda et al Anal. Biochem 1994; 217:167-75. 75 uL of dilution buffer (50 mM Sodium Acetate pH$^-$ 5.8. 0.5% Triton X-100) was added to each well of a 96 well plate (Millipore Multiscreen 96-well filtration system, Millipore, Billerica, Mass.) 25 uL of each digested cartilage explant sample was then loaded followed by 150 uL of 0.2% alcian blue solution (Alcian Blue 8GX electrophoresis grade, Sigma-Aldrich Inc., St. Louis Mo.) and was allowed to rotate for 1 hour at room temperature. The 96-well plate was then placed over a vacuum-manifold to aspirate the contents of the wells through the screen. The 3×200 uL vacuum washes with wash buffer (50 mM sodium acetate pI-I 5.8, 100 mM sodium sulfate, 50 mM MgCl2) were then performed. The 96-well filtration plate was then completely dried at 57 degrees C. for 5 minutes in a hybridization oven and was exposed to storage phosphor screen for 24 hours (Packard Instrument Company Inc., Meriden. Conn.). Phosphorimaging with Cyclone model A431200 (Packard Instrument Company Inc. Meriden, Conn.) was performed to quantify $^{35}$S uptake by proteoglycans. $^{35}$S uptake by proteoglycans in cartilage explants was normalized to DNA by Quant-iT ds DNA Assay Kit (Invitrogen Inc., Carlsbad Calif.).

Results

Effect of Anthocyanins on Normal Cartilage.

The effect of cyanidin on bovine cartilage explants was tested. The dose response was also determined. Cartilage explants were treated with 1L-1 (50 ng/mL) for 24 hours. IL-1 reduces matrix synthesis and induces an inflammatory respond similar to osteoarthritis. Explants were then treated with cyanidin chloride at either 200 or 500 uM concentration for 24 hours. Matrix synthesis was monitored by measuring uptake of $^{35}$S. Although the initial experiment was promising (FIG. 9), we could not reproduce this effect in several subsequent experiments (2 representative results are shown in FIGS. 10 and 11).

Effect of Glucose Concentration and Anthocyanins.

Bovine explants were initially subjected to IL-1 treatment for 24 hours. Explants were then treated with 500 uM cyanidin chloride in a low glucose (1 g/L) or high glucose concentration (4.5 g/L). Overall the combination of cyanidin treatment and high glucose increased matrix synthesis the most (FIG. 12). The higher the glucose concentration increased matrix synthesis by 10%. The cyanidin treatment had small effect under low glucose conditions, but the effect was nearly 20% greater in the high glucose condition.

Effect of Anthocyanins on Osteoarthritic Human Cartilage.

Figure 13:
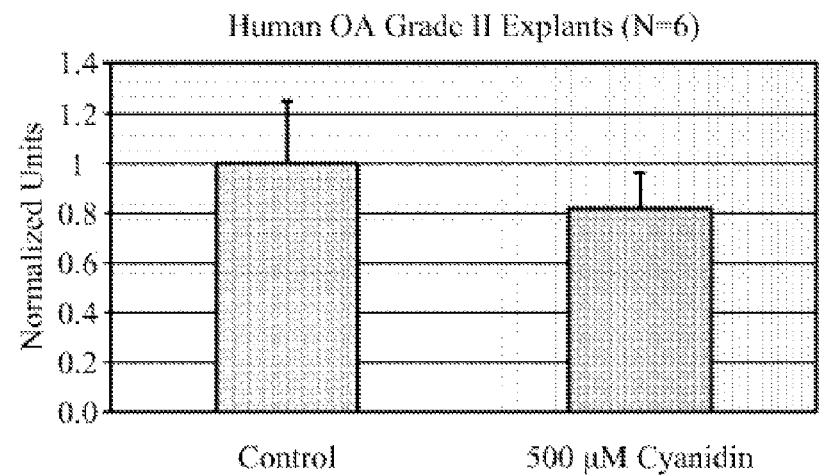
FIG. 13 depicts a chart summarizing the measurement of matrix synthesis in human osteoarthritic cartilage grade II-III explants using $^{35}S$ uptake analysis after treatment with 500 uM cyanidin chloride.

IL-1 treatment mimics some of the biochemical effects of arthritis. However, for clinically relevant validation, and to avoid any effect due to different species, we chose to use human osteoarthritic cartilage for the next series of experiments. Cyanidin did not increase matrix synthesis in human OA tissue (FIG. 13).

Effect of Supraphysiologic Glucose Concentration.

Reported clinical experiments indicate that 10% dextrose injected in the joint can have a therapeutic effect on osteoarthritis. To test this effect, human osteoarthritic cartilage explants (Grade II) were treated with glucose at physiologic (0.45%) or were treated with supraphysiologic (2.5% and 5%) concentrations with 500 uM cyanidin chloride. At 0.45% glucose concentration cyanidin chloride had no effect on matrix synthesis. Supraphysiologic glucose concentration suppressed matrix synthesis (probably because of the increased osmolar tension (FIG. 14).

Example 4: Increasing Glucose Concentration Increases IGF-1 Expression from the Synovial Membrane There is some clinical evidence to suggest that 10% dextrose injected into a joint may have a therapeutic effect on osteoarthritis. We hypothesized that the increased sugar concentration may stimulate the synovium cells to secrete anabolic growth factors that would have a therapeutic effect on degenerating cartilage. To test this hypothesis we harvested synovial tissue from patients undergoing total knee arthroplasty and exposed it to different concentrations of glucose. We selected IGF-1 as the most likely to respond to glucose and measured gene expression as well as protein release in the culture media.

Increasing glucose concentration consistently increased IGF-1 gene expression in synovial tissue. Increasing glucose concentration increased IGF-1 secretion in synovial tissue, but in a donor dependent fashion.

Materials and Methods

Tissue Source and Harvest.

Synovial explants (N=6) were harvested from human donors undergoing either uni-compartmental or total knee replacement. In all but the first experiment, the specimens were trimmed of extraneous adipose tissue and washed in low glucose DMEM (1 g/l). The specimens in the first experiment were not trimmed of excess adipose tissue and were washed in high-glucose DMEM (4.5 g/L).

Glucose Treatment.

In the first experiment (n=2), the specimens were cultured for 48 hours in 0.1% calf serum and either high- or low-glucose DMEM. In the second tow experiments (n=4), the specimens were cultured for 48 hours in serum-free ITS (Insulin, Transferrin, Selenium) media diluted with either high- or low-glucose DMEM. IGF-1 gene expression. Briefly, total RNA was extracted from synovial tissue using RNeasy Total RNA Kit (Qiagen, Inc., Santa Clarita, Calif.). Real-time quantitative RT-PCR was done using Taqman RT-PCR reagents (Applied Biosystems, Foster City, Calif.).

Expression of IGF-1 was normalized to that of the housekeeping gene GAPDH. IGF-1 ELISA. Human IGF-1 protein secretion into the culture media was measured by ELISA (RD Systems, Minneapolis, Minn.). Synovial culture media was centrifuged to remove any particulates. Controls and samples were added to ELISA wells which were pre-coated with a monoclonal antibody specific for IGF-1. Any IGF-1 present would be expected to be bound by the immobilized antibody. After washing away any unbound substances, an enzyme-linked polyclonal antibody specific for IGF-1 was added to the wells. Following a wash to remove any unbound antibody-enzyme reagent. a substrate solution was added to the wells. The medial developed a color intensity in proportion to the amount of IGF-1 bound in the initial step. Optical density of each well was determined by using a microplate reader set to 450 nm. IGF-1 activity obtained by serial dilution of known protein concentrations.

Results

Increasing Glucose Concentration Increases IGF-1 Gene Expression.

We tested the effect of glucose concentration on synovial tissue explants in three separate experiments (three donors). Synovial tissue explants were treated with media containing either low (1 g/L) or high glucose (4.5 g/L) in media for 48 hours. In all three donors, glucose concentration increased IGF-1 gene expression by up to 5 fold. Results are summarized in FIG. 15.

Increasing Glucose Concentration Increases IGF-1 Secretion.

We tested the effect of glucose concentration on synovial tissue explants in 6 separate experiments (6 donors) Synovial explants were treated with media containing either low (1 g/L) or high glucose (4.5 g/L) in media for 48 hours. On average, IGF-1 levels in media more than doubled. However, we noted a donor-dependent response to glucose concentration. In two donors, glucose concentration had no effect on IGF-1 protein release in media, while four donors there was a significant response. Since the tissue came from patients undergoing knee arthroplasty, disease status may play a role. The tissue that responded the most to high glucose (5× increase) came from a donor undergoing unicompartmental arthroplasty and appeared the healthy on visual examination. Results are summarized in FIG. 16.

Example 5: Chondrocyte Toxicity Response to Anthocyanins

Anthocyanins have been shown to have antioxidant effect. Some clinical evidence also suggests that 10% dextrose injected into a joint may have a therapeutic effect on osteoarthritis. In previous experiments, we tested the effects of cyanidin chloride, kuromanin chloride, and 10% dextrose on glycosaminoglycan synthesis rates of bovine chondrocytes suspended in agarose gels. In those experiments, the dose of anthocyanin was arbitrarily chosen. This experiment was designed to assess the cellular toxicity of a range of doses for selected anthocyanin compounds. The objective was to identify the potential range of therapeutic doses in human chondrocytes.

Cyanidin chloride, Kuromanin chloride, Delphinidin-3-O-Glucoside, and Pelargonidin Chloride were non-toxic at concentrations up to 100 uM. Cyanidin chloride, Kuromanin chloride, and Delphinidin-3-O-Glucoside induced cell death at concentrations at or above 200 uM.

Materials and Methods

Cell Source.

Chondrocytes were isolated from non-arthritic regions of adult human articular cartilage (N=3 donors) and expanded in tissue culture flasks in DMEM supplemented with 10% calf serum.

Anthocyanins.

The following compounds were provided by Chromadex, Inc. and tested from 1 uM to 500 uM:
1. Cyanidin chloride
2. Kuromanin chloride
3. Delphinidin-3-O-Glucoside
4. Pelargonidin Chloride MTT Assay.

Human articular chondrocytes were seeded in 96-well culture trays at a density of 5000 cells/well and incubated with the selected concentration of the anthocyanin for 4 days. At the end of the 4 day period, fresh MTT (3(4,5-Dimethylthiazol-2-yl)-2,5-diphenyltetrazolium bromide) was made in PBS and filter sterilized. MTT (25 ul per well) was added to the cell culture and incubated for 5 hours in the $CO_2$ incubator at 37° C. Yellow MIT is reduced to purple formazan in living cells. The supernatant from each well was removed, and 200 Ill of DMSO was added. A multi-channel pipette was used to dissolve crystals. The microplate was placed back into the incubator at 37° C. for 5 min. Formazan levels in each well were read using a spectrophotometer at 550 nm wavelength.

Cell Viability.

At higher concentrations, the color of the anthocyanin interfered with the spectrophotometer reading; therefore, cell viability was additionally measured with calcein staining as follows: Live and dead cells were simultaneously viewed in situ with a confocal microscope (LSM 510; Zeiss, Wetzlar, Germany), using a fluorescent double stain. Calcein AM (1 uM; Invitrogen, Carlsbad, Calif.), a fluorescein derivative that is metabolized by nonspecific esterase present in viable cells, was used to stain live cells. The use of 8 uM ethidium homodimer (Invitrogen), a nucleic acid stain that is excluded by intact cell membranes, enabled visualization of the nuclei of dead cells. After 96-hour exposure to the appropriate concentration of anthocyanins, chondrocytes were cultured in DMEM supplemented with Calcein AM and ethidium homodimer for 45 minutes. Live and dead cells were counted using an automated image analysis script written in Matlab (MathWorks, Natick, Mass.) to measure percentage cell viability.

Results

Figure 17:
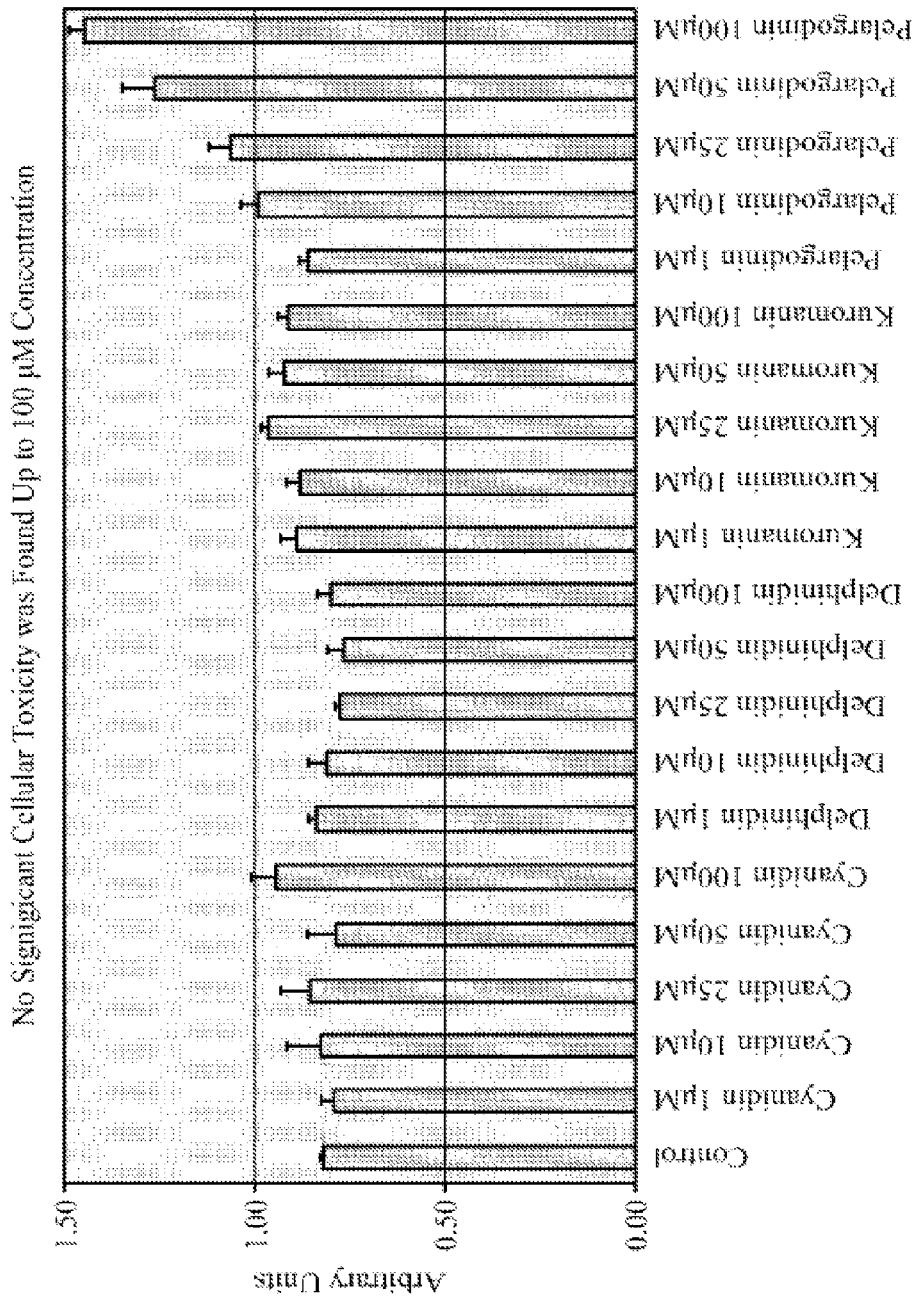
FIG. 17 depicts a chart summarizing the results of a cell toxicity assay testing 100 uM and lower concentrations of cyanidin, delphinidin, kuromanin, and pelargonidin.

No significant cellular toxicity was found at up to 100 uM concentration (MTT assay). We tested the effect of anthocyanin concentration for 96 hours on cells obtained from three donors (FIG. 17). At concentrations greater than 100 uM the anthocyanin changed the color of the media and interfered with the MTT assay reading; therefore, these results are not reported.

Figure 18:
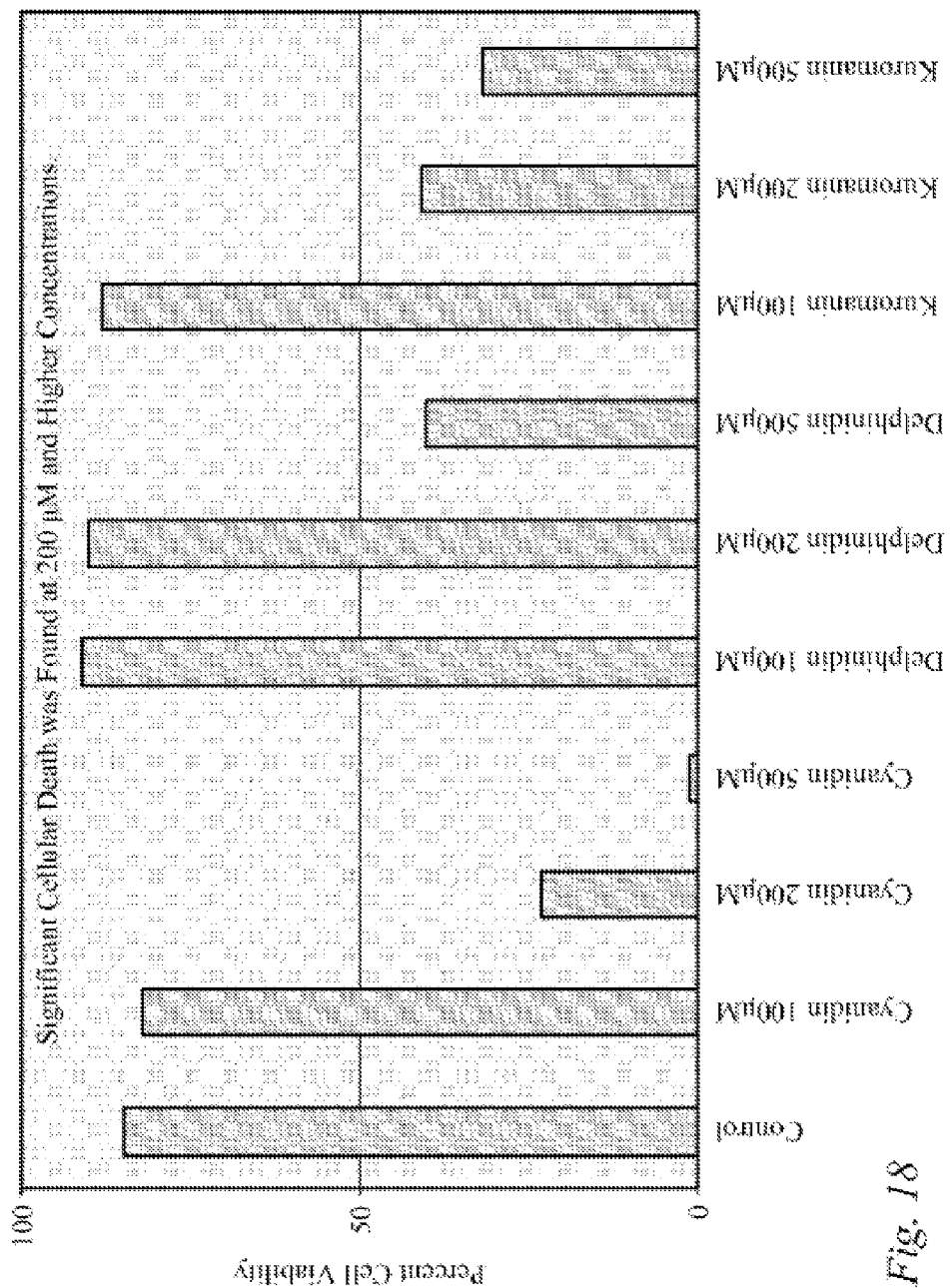
FIG. 18 depicts a chart summarizing the results of a cell toxicity assay testing 200 uM and higher concentrations of cyanidin, delphinidin, kuromanin, and pelargonidin.

Cell viability was found to decrease at concentrations greater than 100 uM concentration. We exposed cells to various concentrations of anthocyanins up to 500 uM for 96 hours. At concentrations greater than 100 μM, the anthocyanin significantly reduced cell viability (FIG. 18). Cyanidin chloride appeared the most toxic, completely reducing cell viability at 500 uM. Delphinidin-3-0-glucoside appeared the least toxic at 200 μM among the compounds tested. Cell viability on exposure to Pelargodinin chloride was not tested because of insufficient quantity.

Example 6: Anthocyanins Detected in Urine but not in Joint after Consumption of Superberries Extract In a published news release, Frei indicated that flavonoids are highly metabolized in the body for rapid excretion in the urine and bile, which alters their chemical structure and diminishes their ability to function as an antioxidant and thus are treated as foreign compounds. (see Background above). Since it is an object of the invention to expose the composition to the synovial joint, anthocyanins were ingested orally and measured after one hour from urine and synovial fluid.

Anthocyanins were detected in the urine but not the synovial fluid. This suggests that there may be a blood synovial barrier to the agent or that the material rapidly metabolized.

Materials and Methods.

A patient suffering from knee pain was orally administered chokeberry extract, which contains anthocyanins, after a 10 hour fast. After 1 hour, both urine and synovial fluid was collected and analyzed for the presence of various anthocyanins.

Results

Anthocyanins were detected in urine but not knee joint. Accordingly, consistent with Frei it is concluded that the anthocyanins were transported from the gut to the kidneys for rapid excretion. Thus, oral administration of anthocyanin would likely require further modification to form an effective oral medication.

Anthocyanins have been shown to have antioxidant effect. Clinical evidence also suggests that 10% dextrose injected into a joint may have a therapeutic effect on osteoarthritis. In previous experiments, we tested the effects of cyanidin chloride, kuromanin chloride, and 10% dextrose on glycosaminoglycan synthesis rates of bovine chondrocytes suspended in agarose gels. In those experiments, the dose of anthocyanin was arbitrarily chosen and later found to be in the range that could be cytotoxic. Subsequently we followed up with experiments to assess the cellular toxicity of a range of doses for selected anthocyanin compounds and identified the highest concentration that was not cytotoxic to human chondrocytes.

In this study we conducted experiments in three models. In one model we analyzed the anabolic effect of anthocyanins on chondrocytes by measuring matrix synthesis rates. In the second model we analyzed the anti-arthritic effect of anthocyanins. IL-1 is a known catabolic cytokine, is highly upregulated in arthritis, and has been implicated as a major factor in cartilage degeneration. IL-1 suppresses matrix synthesis and increases the degradation of existing matrix. By measuring matrix synthesis rates after IL-1 treatment we assessed the effect of anthocyanins in restoring these synthesis rates to normal. TGF-β is one of the most powerful chondrogenic stimuli and significantly increases matrix synthesis rates. With aging there is a substantial reduction in the response to TGF-β. In the third model we determined whether anthocyanins had synergistic effects with TGF-β.

We explored broad therapeutic applications for anthocyanins. An anabolic effect on cartilage would be relevant for increasing the health of cartilage, as a preventive measure for cartilage degeneration, and as an adjunct to cartilage repair and regenerative procedures. An anti-arthritic effect would be directly applicable to the treatment of osteoarthritis. A synergistic effect with growth factors might have therapeutic value in reversing degeneration with aging.

In summary the anthocyanins had no effect on matrix synthesis at 6 hours, delphinidin-3-0-glucoside had an anti-arthritic effect at 12 and 24 hours, and kuromanin chloride had a synergistic effect on matrix synthesis rates at 24 hours when combined with TGF-β

Materials and Methods

Cell Source.

Chondrocytes were isolated from weight-bearing regions of young (18-30 months old) bovine femoral condyles. Primary cells were obtained from 3 different animals and suspended in beads of 2% alginate. The alginate beads were precultured in DMEM supplemented with 10% calf serum for 48 hours. Before the experiments, the chondrocytes were serum-starved overnight with 0.1% serum to reduce the effect of serum and to reduce anabolic activity to baseline. Anthocyanins. The following compounds were used:
Cyanidin chloride (100 uM)
Kuromanin chloride (100 uM)
Delphinidin-3-O-Glucoside (100 uM)

Matrix Synthesis Rate.

For each treatment condition, 10 millicuries of $^{35}$S was added to each well and incubated for the appropriate duration. At the appropriate harvest time point, each well was then washed extensively with PBS (5-6 times with 500 uL of PBS), before trypsin and EDTA was added to dissolve alginate. After 20-30 minutes, the dissolved gels and released cells were transferred into 1.5 ml Eppendorf tubes with 150 uL of calf serum (to promote pellet formation) and the cells were centrifuged at 2000 rpm for 5 minutes. The supernatant was removed via pipette without disturbing the cell pellet. The remaining cell and supernatant (approximately 300 ul) was then mixed with 500 uL of PBS and transferred to scintillation vials, to which 5 ml of scintillation fluid was dispensed. Each scintillation vial was capped, thoroughly vortexed and then placed in a gamma counter to measure gamma radiation emission for each sample. Each sample was measured for 5 minutes.

Study Design

TABLE 2

Anabolic Effect

| Experimental Groups | $^{35}$S uptake | | |
|---|---|---|---|
| Control | 6 hours | 12 hours | 24 hours |
| Cyanidin chloride | 6 hours | 12 hours | 24 hours |
| Kuromanin chloride | 6 hours | 12 hours | 24 hours |
| Delphinidin-3-O-Glucoside | 6 hours | 12 hours | 24 hours |

TABLE 3

Anti-arthritic Effect

| Experimental Groups | $^{35}$S uptake | | |
|---|---|---|---|
| Control + IL-1 5 ng/mL | 6 hours | 12 hours | 24 hours |
| Cyanidin chloride + IL-1 5 ng/mL | 6 hours | 12 hours | 24 hours |
| Kuromanin chloride + IL-1 5 ng/mL | 6 hours | 12 hours | 24 hours |
| Delphinidin-3-O-Glucoside + IL-1 5 ng/mL | 6 hours | 12 hours | 24 hours |

TABLE 4

Growth Factor Synergy

| Experimental Groups | 35 |
|---|---|
| Control + TGF-β + 10 ng/mL | 24 hours |
| Cyanidin chloride + TGF-β 10 ng/mL | 24 hours |
| Kuromanin chloride + TGF-β 10 ng/mL | 24 hours |
| Delphinidin-3-O-Glucoside + TGF-β 10 ng/mL | 24 hours |

Results

Figure 19A:
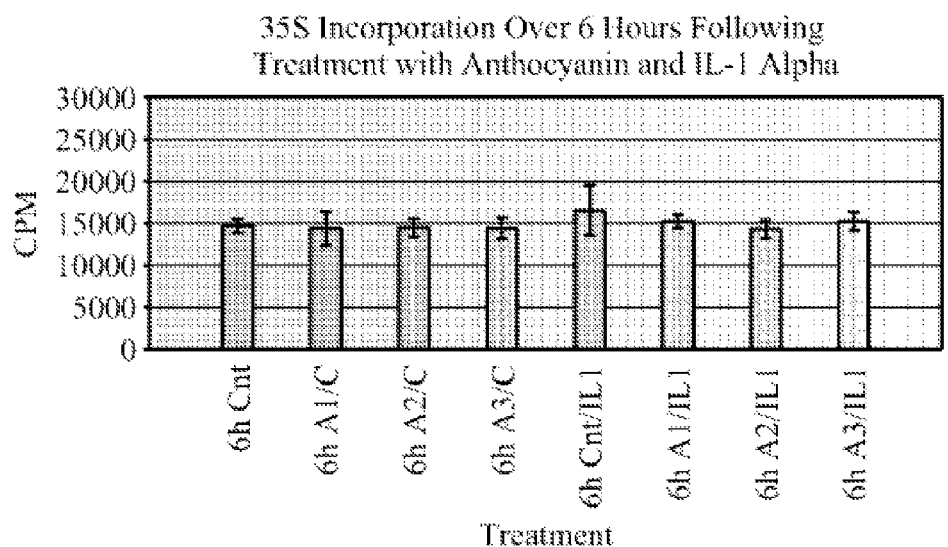
FIG. 19a-c depicts a chart of a time course experiment measuring the uptake of $^{35}S$ in cartilage explants over 6 hours (FIG. 19a), 12 hours (FIG. 19b) and 24 hours (FIG. 19c) following treatment with anthocyanin and IL-1 alpha. A1 represents cyanidin chloride; A2 represents delphinidin-3-O-glucoside; A3 represents kuromanin chloride; IL-1 represents interleukin-1; and Cnt represents control or no anthocyanin.
Figure 20:
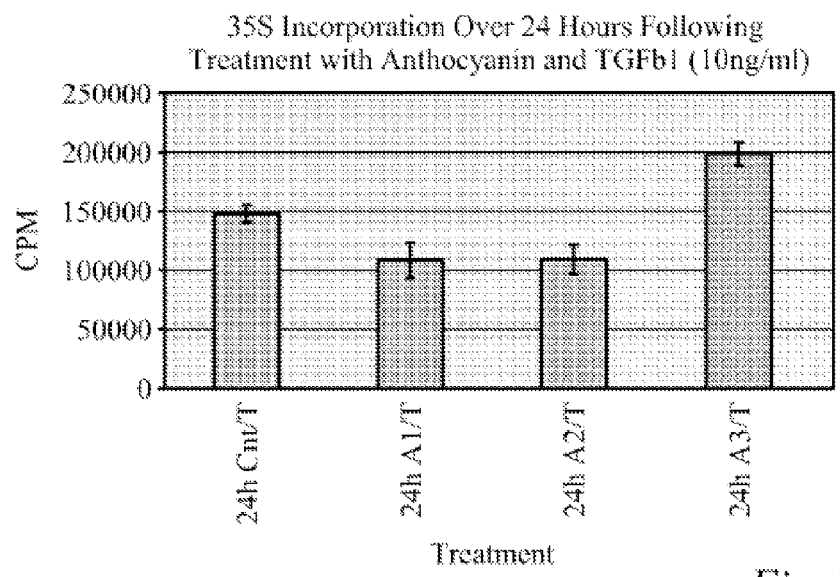
FIG. 20 depicts a chart demonstrating $^{35}S$ incorporation of cartilage explants over 24 hours following treatment with anthocyanin and TGF beta (TGF-β). A1 represents cyanidin chloride; A2 represents delphinidin-3-O-glucoside; A3 represents kuromanin chloride; T represents TGF-β; and Cnt represents control or no anthocyanin.

Referring to FIG. 19a, No significant increase in matrix synthesis rates with anthocyanin treatment was noted at 6 hours. (A1: Cyanidin chloride, A2: Delphinidin-3-O-glucoside, A3: Kuromanin Chloride, Cnt=no anthocyanins, C=no IL1, IL1=Interleukin 1α, T=TGF-β).

Figure 19B:
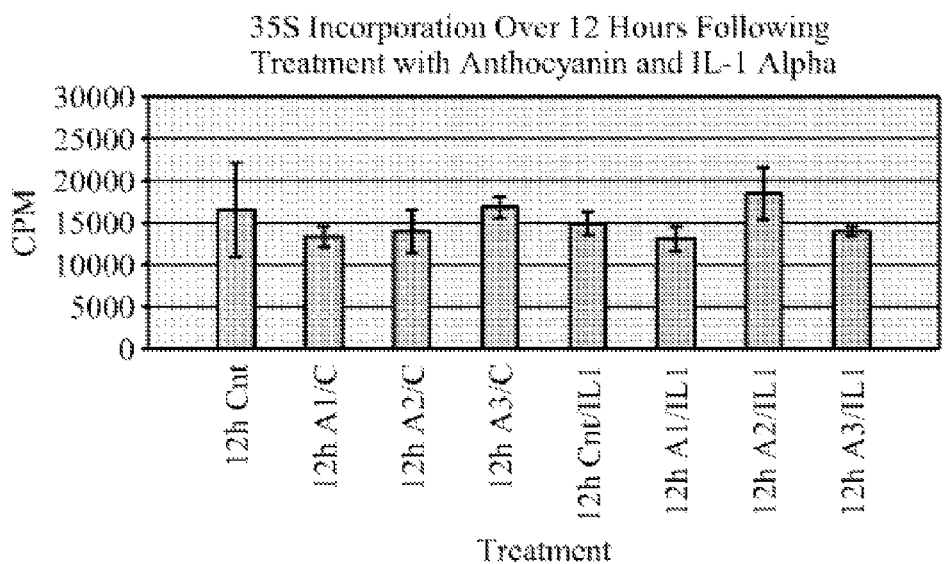

Referring to FIG. 19b, IL-1 treatment suppressed matrix synthesis rates by 12 hours. Delphinidin-3-O-glucoside reversed the effect of IL-1 suppression on matrix synthesis rates. (A1: Cyanidin chloride, A2: Delphinidin-3-O-glucoside, A3: Kuromanin Chloride, Cnt=no anthocyanins, C=no IL1, IL1=Interleukin 1α, T=TGF-β

Figure 19C:
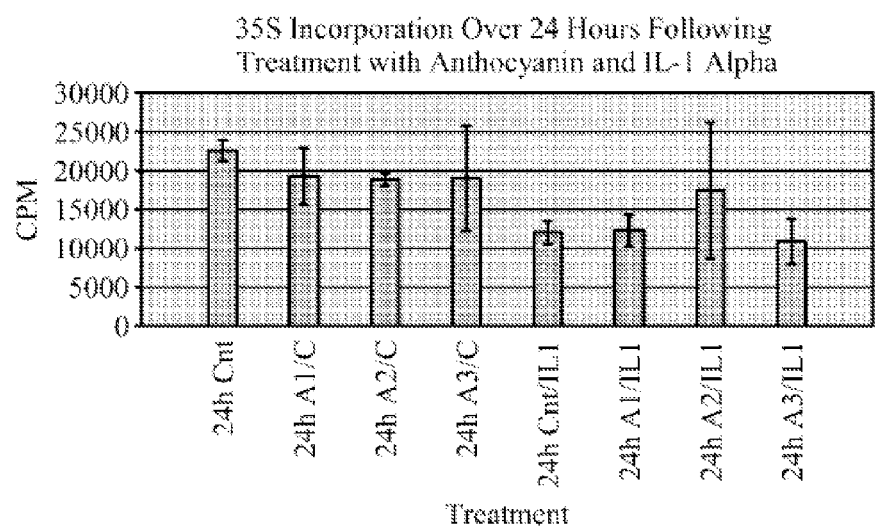

Referring to FIG. 19c, IL-1 treatment suppressed matrix synthesis rates by 24 hours. Delphinidin-3-O-glucoside reversed the effect of IL-1 suppression on matrix synthesis rates. (A1: Cyanidin chloride, A2: Delphinidin-3-O-glucoside, A3: Kuromanin Chloride, Cnt=no anthocyanins, C=no IL-1, IL1=Interleukin 1α, T=TGF-β)

Referring to FIG. 20, Kuromanin Chloride had a synergistic effect on matrix synthesis rates when combined with TGF-β. (A1: Cyanidin chloride, A2: Delphinidin-3-O-glucoside, A3: Kuromanin Chloride, Cnt:=no anthocyanins, T: TGF-β).

Example 7: Effects of Glucose and Anthocyanin on IGF-1 in Synovium

There is some clinical evidence to suggest that 10% dextrose injected into a joint may have a therapeutic effect on osteoarthritis. We hypothesized that the increased sugar concentration may stimulate the synovium cells to secrete anabolic growth factors that would have a therapeutic effect on degenerating cartilage. To test this hypothesis we harvested synovial tissue from patients undergoing total knee arthroplasty and exposed it to different concentrations of glucose. We selected insulin-like growth factor as the most likely to respond to glucose and measured gene expression as well as protein release in the culture media.

In addition, there is evidence in the literature that various anthocyanins trigger the release of insulin from the kidney. We hypothesized that, due to the various overlaps in the glucose-insulin IGF pathway, Anthocyanins may also have similar effects on IGF-1 in the synovium.

Although not shown, the cycles of IGF-1 gene expression analyzed by PCR were in the 30's, compared to the housekeeping gene GAPDH, which was in the teens. Thus, the IGF-1 gene is expressed in the synovium, albeit at low levels. Higher levels of IGF-1 protein were found in the media with larger and better quality samples. The most consistent increase in IGF-I protein expression is with High Glucose alone. It appears that anthocyanins can increase the level of IGF-1 protein or gene expression. However, which anthocyanin and whether it is improved with the addition of glucose remains currently undefined.

Materials and Methods

Tissue Source and Harvest.

Synovial explants (n=6) were harvested from human donors undergoing total knee replacement. The specimens were trimmed of extraneous adipose tissue. In the two experiments, the synovial specimens were washed in low-glucose DMEM (1 g/L) for a few hours and then placed in the assigned treatment groups. In subsequent experiments the synovial specimens were washed in low-glucoses DMEM for 24 hours before treatment.

Treatment Groups.

In all experiments (n=4), the specimens were cultured for 48 hours in serum-free ITS (Insulin, Transferrin, Selenium) media diluted with either high- or low-glucose DMEM. In addition, various anthocyanins were added to both the high- and low-glucose groups. Low-glucose alone acted as a control group. After the two experiments, the level of media was adjusted relative to the weight of the tissue.

IGF-1 Gene Expression.

Briefly, total RNA was extracted from synovial tissue using RNeasy Total RNA Kit (Qiagen Inc., Santa Clarita, Calif.). Real-time quantitative RT-PCR was done using 'ragman RT-PCR. reagents (Applied Biosystems, Foster City, Calif.). Expression of IGF-1 was normalized to that of the housekeeping gene GAPDH. The results of IGF-1 gene expression are only presented if detectable levels of low glucose alone were present and able to serve as a control group for relative-fold change in expression.

IGF-1 ELISA.

Human IGF-1 protein secretion into the culture media was measured by ELISA (R & D Systems, Minneapolis, Minn.). Synovial culture media was centrifuged to remove any particulates. Controls and samples were added to ELISA wells which were pre-coated with a monoclonal antibody specific for IGF-1. Any IGF-1 present would be expected to be bound by the immobilized antibody. After washing away any unbound substances, an enzyme-linked polyclonal antibody specific for IGF-1 was added to the wells. Following a wash to remove any unbound antibody-enzyme reagent, a substrate solution was added to the wells. The media developed a color intensity in proportion to the amount of IGF-1 bound in the initial step. Optical density of each well was determined by using a microplate reader set to 450 nm. IGF-1 concentration in the sample was calculated by a standardized curve of IGF-I activity obtained by serial dilution of known protein concentrations.

Results

Figure 21:
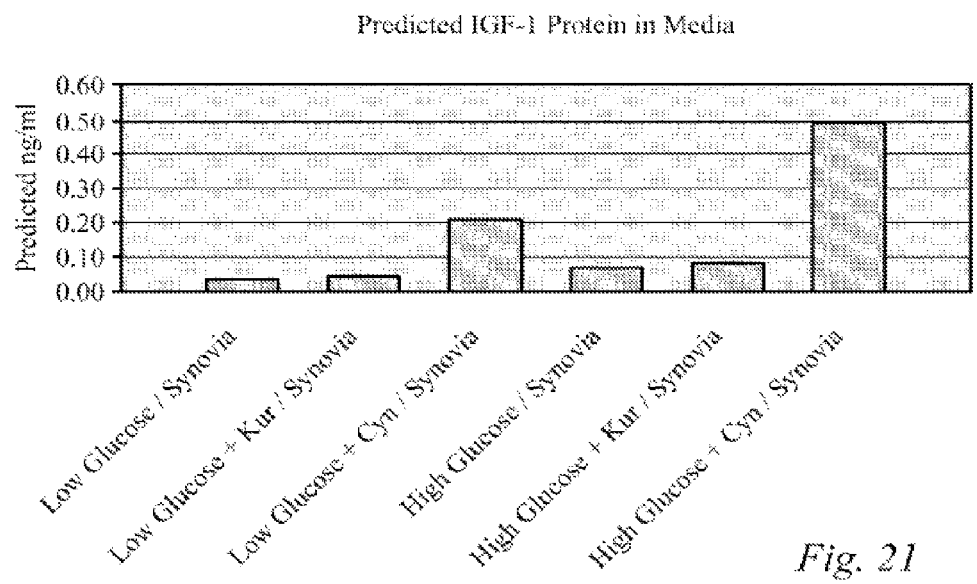
FIG. 21 depicts a graph demonstrating the predicted amount of IGF-1 protein in media after treatment of synovial explants with varying concentrations of anthocyanin and glucose.

Referring to FIG. 21, the predicted level of IGF-1 using 7 ml of media per sample regardless of sample weight. It appears that High Glucose plus Cyanidin has the highest IGF-1 protein levels in this experiment.

Figure 22:
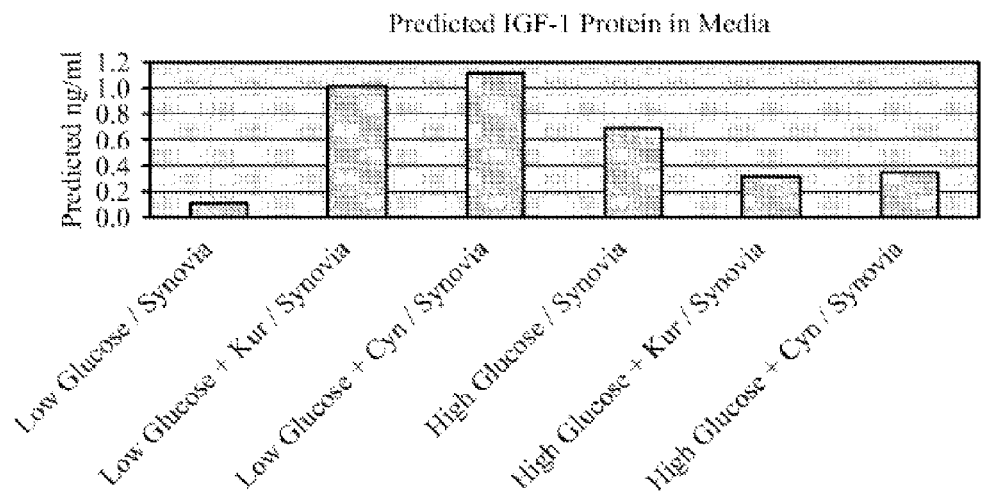
FIG. 22 depicts a graph demonstrating the predicted amount of IGF-1 protein in media after treatment of synovial explants with varying concentrations of anthocyanin and glucose titrated to match tissue weight.

Referring to FIG. 22, the levels of IGF-1 protein with volume levels titrated to match the weight of the tissue. In this experiment, the two anthocyanins (Kuromanin and Cyanidin) combined with low glucose had the greatest effect. The effect of the anthocyanins in high glucose appear to be inhibitory.

Figure 23:
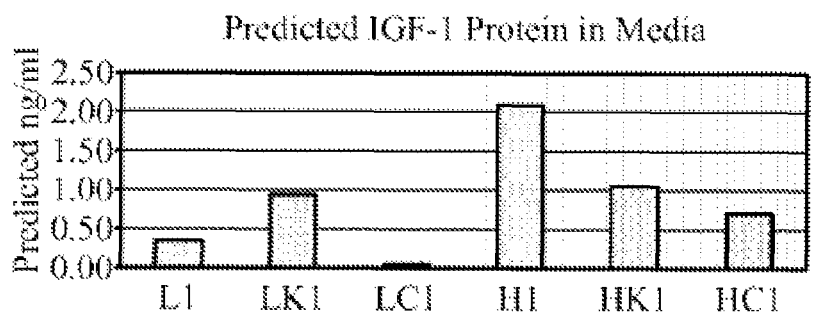
FIG. 23 depicts a graph demonstrating the predicted amount of IGF-1 protein in media of another experiment after treatment of synovial explants with varying concentrations of anthocyanin and glucose.

Referring to FIG. 23, the levels of IGF-1 protein with volume levels titrated to match the weight of the tissue. The highest level of IGF-1 protein was found with High Glucose alone, reaching above 2.00 ng/ml.

Figure 24:
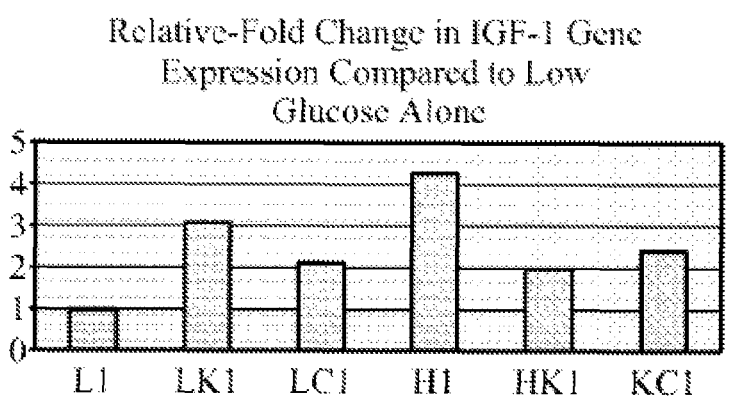
FIG. 24 depicts a graph demonstrating the relative fold change in IGF-1 gene expression compared to low glucose alone.

Referring to FIG. 24, the relative-fold change in IGF-1 gene expression for each sample was compared to low glucose alone. High glucose alone had over 4-fold greater expression than low glucose alone. Kuromanin showed 3-fold greater expression in the presence of low glucose. In the presence of high glucose, the effect of Kuromanin appears to be inhibitory.

Figure 25:
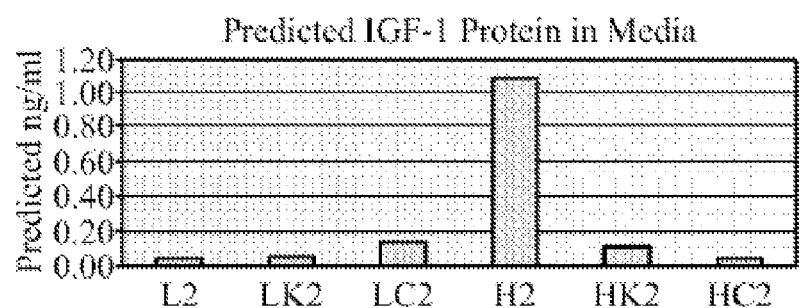
FIG. 25 depicts a graph demonstrating the predicted amount of IGF-1 protein in media after treatment of synovial explants with varying concentrations of anthocyanin and glucose titrated to match tissue weight.

Referring to FIG. 25, the levels of IGF-1 protein with volume levels titrated to match the weight of the tissue. The highest level of IGF-1 protein was found with High Glucose alone.

Figure 26:
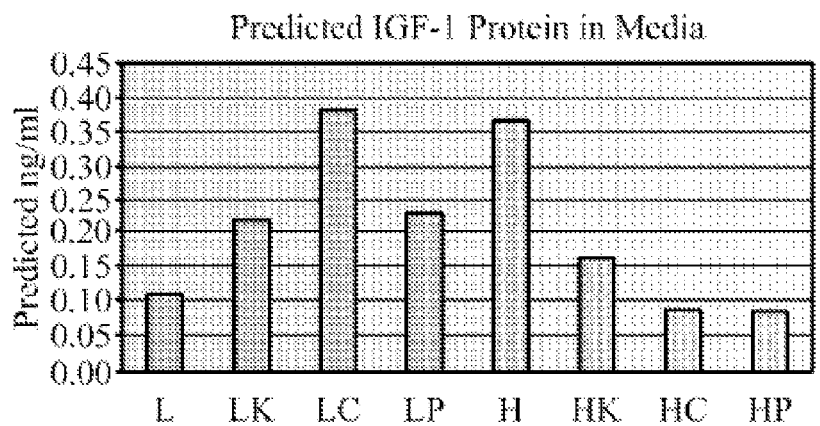
FIG. 26 depicts a graph demonstrating the predicted amount of IGF-I protein in media after treatment of synovial explants with varying concentrations of anthocyanin (lower concentrations) and glucose titrated to match tissue weight.

Referring to FIG. 26, the levels of IGF-1 protein with volume levels titrated to match the weight of the tissue. This particular experiment used lower concentrations of anthocyanins (5 mM vs previous 50 mM). The highest level of IGF-1 protein was found with Cyanidin in the presence of low glucose and with High Glucose alone.

Figure 27:
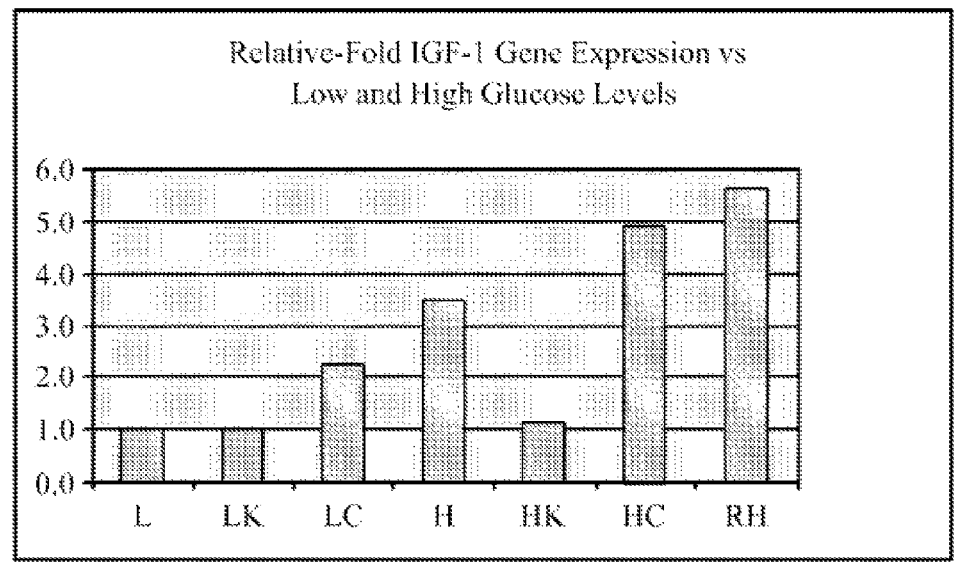
FIG. 27 depicts a graph demonstrating the relative-fold IGF-1 gene expression in synovial explants compared to varied glucose levels.

Referring to FIG. 27, the relative-fold change in IGF-1 gene expression for each sample was compared to low glucose alone. The highest expression levels were found with the Cyanidin in the presence of high glucose and High Glucose alone with a sample that appeared grossly inflamed and "more reactive" (RH).

Figure 28:
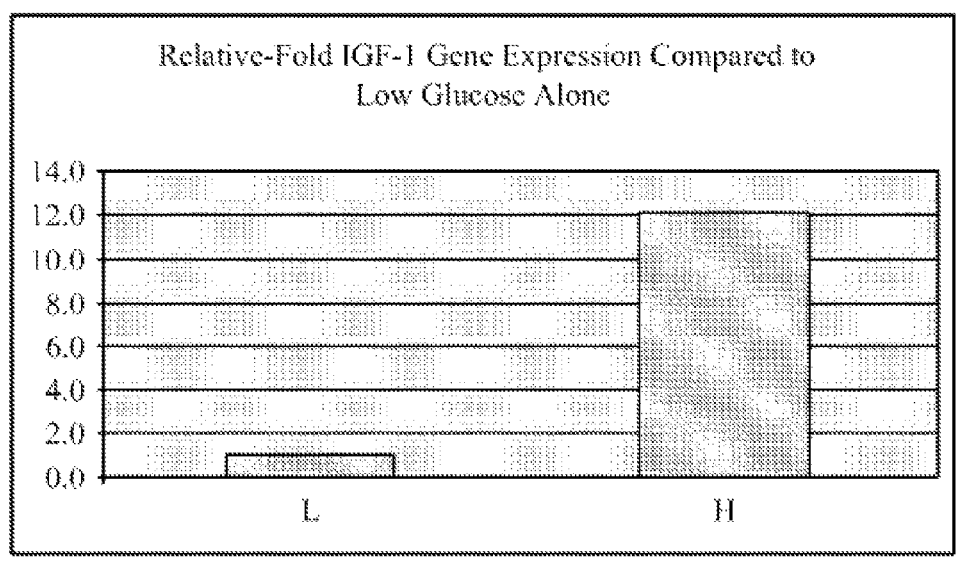
FIG. 28 depicts a graph demonstrating the relative-fold IGF-1 gene expression in synovial explants compared to low glucose alone.

Referring to FIG. 28, the relative-fold change in IGF-1 gene expression for each sample compared to low glucose alone. Only High and Low Glucose were run, as the sample was out of media for several hours from the OR and thus initial assays were run to save time and expense. High Glucose alone appears to have a 12-fold increase in IGF-1 gene expression.

What is claimed is:

1. A method of inhibiting interleukin-1 (IL-1) induced glycosaminoglycoside (GAG) release in an arthritic joint of a subject, comprising administering into the arthritic joint of the subject by an intra-articular injection, a composition comprising cyanidin-3-glucoside (C3G), glucose and a pharmaceutically acceptable carrier, wherein the concentration of glucose is about 5%, and wherein the C3G is administered at a dose of 0.002 mg to 100 mg per joint that is effective to elicit the inhibition of IL-1 induced GAG release in the arthritic joint of the subject.

2. The method according to claim 1, wherein the composition increases expression of IGF-1 in the arthritic joint.

3. The method according to claim 2, wherein the composition is provided in a biodegradable microsphere.

4. The method according to claim 3, wherein the biodegradable microsphere comprises a slow release bioabsorbable material.

5. The method according to claim 4, wherein the bioadsorbable material is 50/50 D, L lactide/glycolide or 85/15 D, L lactide/glycolide.

6. The method according to claim 1, wherein the composition has a chondroprotective and/or chondronutritive effect in the joint of a subject.

7. The method of claim 1, wherein the composition treats damaged cartilage in the arthritic joint.

8. The method of claim 1, wherein the joint is a synovial joint.

9. The method of claim 7, wherein the injection comprises the formation of anthocyanin metabolites in the synovial fluid.

10. The method according to claim 1, wherein the dose of 0.002 mg to 100 mg per joint of C3G is provided at a concentration not exceeding about 100 μM.

11. The method according to claim 1, wherein the composition is administered with IGF-1, insulin, or a mixture thereof.

12. A method for treating damaged cartilage in an arthritic joint in a subject, comprising administering into the arthritic joint of the subject, by an intra-articular injection, a composition that is a solution comprising an anthocyanin, glucose and a pharmaceutically acceptable carrier, wherein the concentration of the glucose is about 0.5% to about 10%;
wherein the anthocyanin is cyanidin-3-glucoside (C3G), and wherein the C3G is administered at a dose of 0.002 mg to 100 mg per joint.

13. The method according to claim 12, wherein the composition increases production of insulin-like growth factor-1 (IGF-1) in the joint.

14. The method according to claim 12, wherein the glucose is administered at about 5%.

15. The method according to claim 12, wherein the glucose is administered at about 10%.

16. The method of claim 12, wherein the joint is a synovial joint.

17. The method according to claim 12, wherein the composition is administered with IGF-1, insulin, or a mixture thereof.

18. The method according to claim 12, wherein the composition is provided in a biodegradable microsphere.

19. The method according to claim 18, wherein the microsphere comprises a slow release bioabsorbable material.

20. The method according to claim 19, wherein the bioabsorbable material is 50/50 D, L lactide/glycoside, or 85/15 D, L lactide/glycolide.

* * * * *